United States Patent
Brooks et al.

(10) Patent No.: US 7,329,406 B2
(45) Date of Patent: *Feb. 12, 2008

(54) METHODS OF TREATING PSORIASIS WITH $\alpha_v\beta_3$-SPECIFIC ANTIBODIES

(75) Inventors: Peter C. Brooks, Carmel, NY (US); David A. Cheresh, Encinitas, CA (US)

(73) Assignee: The Scripps Research Institute, La Jolla, CA (US)

( * ) Notice: Subject to any disclaimer, the term of this patent is extended or adjusted under 35 U.S.C. 154(b) by 382 days.

This patent is subject to a terminal disclaimer.

(21) Appl. No.: 10/892,653

(22) Filed: Jul. 15, 2004

(65) Prior Publication Data

US 2004/0258691 A1    Dec. 23, 2004

Related U.S. Application Data

(60) Division of application No. 09/081,522, filed on May 19, 1998, now Pat. No. 6,887,473, which is a continuation of application No. 08/210,715, filed on Mar. 18, 1994, now Pat. No. 5,753,230.

(51) Int. Cl.
*A61K 39/395* (2006.01)
*C07K 16/28* (2006.01)

(52) U.S. Cl. .............................. 424/152.1; 424/130.1; 424/133.1; 424/141.1; 424/143.1; 424/172.1; 530/387.1; 530/387.3; 530/388.1; 530/388.2; 530/388.22

(58) Field of Classification Search ............... None
See application file for complete search history.

(56) References Cited

U.S. PATENT DOCUMENTS 5,753,230 A * 5/1998 Brooks et al. ........... 424/158.1

FOREIGN PATENT DOCUMENTS

EP      1 334 730 A2    8/2003

OTHER PUBLICATIONS

Communication of a Notice of Opposition to European Patent 0 754 059, Sep. 30, 2004.
Cheresh, et al., "Arg-Gly-Asp Recognition by a Cell Adhesion Receptor Requires Its 130-kDa α Subunit", *J. Bio. Chem. 262* (4): 1434-1437 (1987).
Grant, et al., "Two Different Laminin Domains Mediate the Differentiation of Human Endothelial Cells into Capillary-like Structures in Vitro", *Cell 58*: 933-943 (1989).

* cited by examiner

*Primary Examiner*—Phillip Gambel
(74) *Attorney, Agent, or Firm*—Hugh Wang; Thomas Fitting

(57) ABSTRACT

The present invention describes methods for inhibition angiogenesis in tissues using vitronectin $\alpha_v\beta_3$ antagonists, and particularly for inhibiting angiogenesis in inflamed tissues and in tumor tissues and metastases using therapeutic compositions containing $\alpha_v\beta_3$ antagonists.

11 Claims, 12 Drawing Sheets

Normal Skin   Granulation Tissue

Anti-$\beta_3$

Anti-$\beta_1$

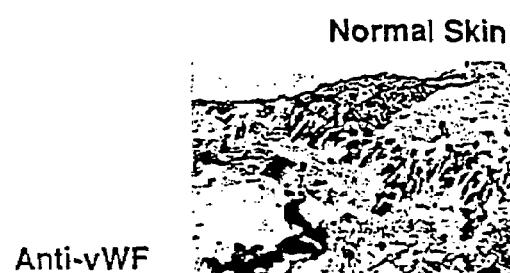
FIGURE 2A     FIGURE 2B
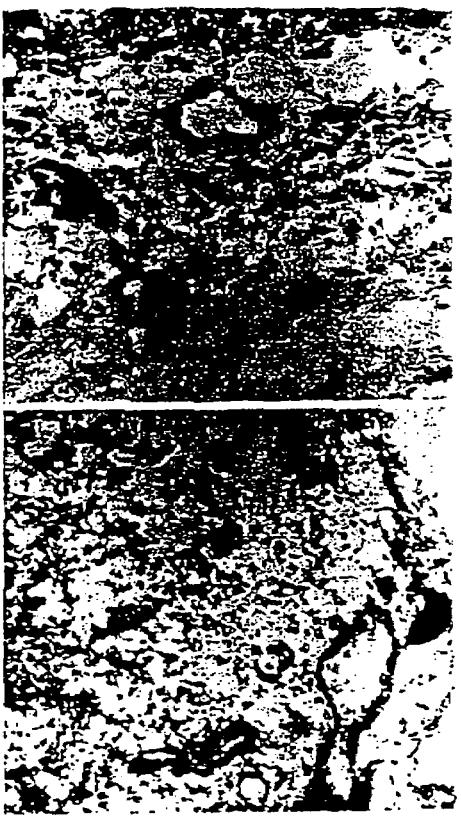
FIGURE 2C     FIGURE 2D

Bladder cancer

Colon Cancer

Breast Cancer

Lung cancer

Untreated
Anti-$\beta_1$

Untreated
Anti-$\alpha v\beta_3$ bFGF Treated
Anti-$\alpha v\beta_3$

Control   bFGF   TNFα

Control Peptide Tumor

Cyclic RGD Tumor

Cyclic RGD Adjacent CAM

FIGURE 10C Anti-αVβ3 (LM609)
FIGURE 10B Anti-αVβ5 (P3G2)
FIGURE 10A Control Anti-β1

Anti-αvβ5

Anti-αvβ3

METHODS OF TREATING PSORIASIS WITH $\alpha_v\beta_3$-SPECIFIC ANTIBODIES

This application is a divisional of application Ser. No. 09/081,522, filed May 19, 1998, now issued as U.S. Pat. No. 6,887,473, which is a continuation of application Ser. No. 08/210,715, filed Mar. 18, 1994, now issued as U.S. Pat. No. 5,753,230. The disclosures of the foregoing applications are hereby incorporated by reference herein.

This invention was made with government support under Contract No. CA 45726 by the National Institute of Health. The government has certain rights in the invention.

TECHNICAL FIELD

The present invention relates generally to the field of medicine, and relates specifically to methods and compositions for inhibiting angiogenesis of tissues using antagonists of the vitronectin receptor $\alpha_v\beta_3$.

BACKGROUND

Integrins are a class of cellular receptors known to bind extracellular matrix proteins, and therefore mediate cell-cell and cell-extracellular matrix interactions, referred generally to cell adhesion events. However, although many integrins and the ligands that bind an integrin are described in the literature, the biological function of many of the integrins remains elusive. The integrin receptors constitute a family of proteins with shared structural characteristics of noncovalent heterodimeric glycoprotein complexes formed of $\alpha$ and $\beta$ subunits.

The vitronectin receptor, named for its original characteristic of preferential binding to vitronectin, is now known to refer to three different integrins, designated $\alpha_v\beta_1$ $\alpha_v\beta_3$ and $\alpha_v\beta_5$. Horton, *Int. J. Exp. Pathol.*, 71:741-759 (1990). $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteospontin and bone sialoprotein I. $\alpha_v\beta_5$ binds vitronectin. The specific cell adhesion roles these three integrins play in the many cellular interaction in tissues is still under investigation, but it is clear that there are different integrins with different biological functions.

One important recognition site in the ligand for many integrins is the arginine-glycine-aspartic acid (RGD) tripeptide sequence. RGD is found in all of the ligands identified above for the vitronectin receptor integrins. This RGD recognition site can be mimicked by polypeptides ("peptides") that contain the RGD sequence, and such RGD peptides are known inhibitors of integrin function. It is important to note, however, that depending upon the sequence and structure of the RGD peptide, the specificity of the inhibition can be altered to target specific integrins.

For discussions of the RGD recognition site, see Pierschbacher et al., *Nature*, 309:30-33 (1984), and Pierschbacher et al., *Proc. Natl. Acad. Sci. USA*, 81:5985-5988 (1984). Various RGD polypeptides of varying integrin specificity have also been described by Grant et al., *Cell*, 58:933-943 (1989), Ruggeri et al., and Aumailley et al., *FEBS Letts.*, 291:50-54. (1991), and in U.S. Pat. Nos. 4,517,686, 4,578,079, 4,589,881, 4,614,517, 4,661,111, 4,792,525, 4,683,291, 4,879,237, 4,988,621, 5,041,380 and 5,061,693.

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: The vessels can sprout from pre-existing vessels, de-novo development of vessels can arise from precursor cells (vasculogenesis), or existing small vessels can enlarge in diameter. Blood et al., *Bioch. Biophys. Acta*, 1032:89-118 (1990). Vascular endothelial cells are known to contain at least five RGD-dependent integrins, including the vitronectin receptor ($\alpha_v\beta_3$ or $\alpha_v\beta_5$), the collagen Types I and IV receptor ($\alpha_1\beta_1$), the laminin receptor ($\alpha_2\beta_1$), the fibronectin/laminin/collagen receptor ($\alpha_3\beta_1$) and the fibronectin receptor ($\alpha_5\beta_1$). (Davis et al., *J. Cell. Biochem.*, 51:206-218 (1993). The smooth muscle cell is known to contain at least six RGD-dependent integrins, including $\alpha_5\beta_1$, $\alpha_v\beta_3$ and $\alpha_v\beta_5$.

Angiogenesis is an important process in neonatal growth, but is also important in wound healing and in the pathogenesis of a large variety of clinical diseases including tissue inflammation, arthritis, tumor growth, diabetic retinopathy, macular degeneration by neovascularization of retina and the like conditions. These clinical manifestations associated with angiogenesis are referred to an angiogenic diseases. Folkman et al., *Science*, 235:442-447 (1987). Angiogenesis is generally absent in adult or mature tissues, although it does occur in wound healing and in the corpeus leuteum growth cycle. See, for example, Moses et al., *Science*, 248:1408-1410 (1990).

It has been proposed that inhibition of angiogenesis would be a useful therapy for restricting tumor growth. Inhibition of angiogenesis has been proposed by (1) inhibition of release of "angiogenic molecules" such as βFGF, (2) neutralization of angiogenic molecules, such as by use of anti-βFGF antibodies, and (3) inhibition of endothelial cell response to angiogenic stimuli. This latter strategy has received attention, and Folkman et al., *Cancer Biology*, 3:89-96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interpheron, and the like that might be used to inhibit angiogenesis. For additional proposed inhibitors of angiogenesis, see Blood et al., *Bioch. Biophys. Acta*, 1032:89-118 (1990), Moses et al., *Science*, 248:1408-1410 (1990), Ingber et al., *Lab. Invest.*, 59:44-51 (1988), and U.S. Pat. Nos. 5,092,885, 5,112,946, 5,192,744, and 5,202,352. None of the inhibitors of angiogenesis described in the foregoing references are targeted at inhibition of $\alpha_v\beta_3$.

RGD-containing peptides that inhibit vitronectin receptor $\alpha_v\beta_3$ have also been described. Aumailley et al., *FEBS Letts.*, 291:50-54 (1991), Choi et al., *J. Vasc. Surg.*, 19:125-134 (1994), and Smith et al., *J. Biol. Chem.*, 265:12267-12271 (1990). However, the role of the integrin $\alpha_v\beta_3$ in angiogenesis has never been suggested nor identified until the present invention.

Inhibition of cell adhesion in vitro using monoclonal antibodies immunospecific for various integrin α or β subunits have implicated $\alpha_v\beta_3$ in cell adhesion of a variety of cell types including microvascular endothelial cells. Davis et al., *J. Cell. Biol.*, 51:206-218 (1993). In addition, Nicosia et al., *Am. J. Pathol.*, 138:829-833 (1991), described the use of the RGD peptide GRGDS (SEQ ID NO 15)to in vitro inhibit the formation of "microvessels" from rat aorta cultured in collagen gel. However, the inhibition of formation of "microvessels" in vitro in collagen gel cultures is not a model for inhibition of angiogenesis in a tissue because it is not shown that the microvessel structures are the same as capillary sprouts or that the formation of the microvessel in collagen gel culture is the same as neo-vascular growth into an intact tissue, such as arthritic tissue, tumor tissue or disease tissue where inhibition of angiogenesis is desirable.

Therefore, other than the studies reported here, Applicants are unaware of any other demonstration that angiogenesis could be inhibited in a tissue using inhibitors of cell adhesion. In particular, it has never been previously demonstrated that $\alpha_v\beta_3$ function is required for angiogenesis in a tissue or that $\alpha_v\beta_3$ antagonists can inhibit angiogenesis in a tissue.

BRIEF DESCRIPTIONS OF THE INVENTION

The present invention disclosure demonstrates that angiogenesis in tissues requires integrin $\alpha_v\beta_3$, and that inhibitors of $\alpha_v\beta_3$ can inhibit angiogenesis. The disclosure also demonstrates that antagonists of other integrins, such as $\alpha_v\beta_5$, or $\alpha_v\beta_1$, do not inhibit angiogenesis, presumably because these other integrins are not essential for angiogenesis to occur.

The invention therefore describes methods for inhibiting angiogenesis in a tissue comprising administering to the tissue a composition comprising an angiogenesis-inhibiting amount of an $\alpha_v\beta_3$ antagonist.

The tissue to be treated can be any tissue in which inhibition of angiogenesis is desirable, such as diseased tissue where neo-vascularization is occurring. Exemplary tissues include inflamed tissue, solid tumors, metastases, and the like tissues.

An $\alpha_v\beta_3$ antagonist for use in the present methods is capable of binding to $\alpha_v\beta_3$ and competitively inhibiting the ability of $\alpha_v\beta_3$ to bind to a natural ligand. Preferably, the antagonist exhibits specificity for $\alpha_v\beta_3$ over other integrins. In a particularly preferred embodiment, the $\alpha_v\beta_3$ antagonist inhibits binding of fibrinogen or other RGD-containing ligands to $\alpha_v\beta_3$ but does not substantially inhibit binding of fibronectin to $\alpha_{IIb}\beta_3$. A preferred $\alpha_v\beta_3$ antagonist can be a polypeptide or a monoclonal antibody, or functional fragment thereof, that immunoreacts with $\alpha_v\beta_3$.

BRIEF DESCRIPTION OF THE DRAWINGS

In the drawings forming a portion of this disclosure:

FIGS. 1A and 1B respectively illustrate the immunoreactivity of anti-$\beta_3$ in normal skin and granulation tissue. FIGS. 1C and 1D respectively illustrate the immunoreactivity of anti-$\beta_1$ in normal skin and granulation tissue.

FIGS. 2A-2D illustrate the tissue distribution of the von Willebrand factor and laminin ligands that respectively bind the $\beta_3$ and $\beta_1$ integrin subunits in normal skin and in skin undergoing wound healing designated as granulation tissue. Immunohistochemistry with antibodies to von Willebrand factor (anti-vWF) and laminin (anti-laminin) was performed as described in Example 3B. FIGS. 2A and 2B respectively illustrate the immunoreactivity of anti-vWF in normal skin and granulation tissue. FIGS. 2C and 2D respectively illustrate the immunoreactivity of anti-laminin in normal skin and granulation tissue.

FIG. 5A shows the distribution of the $\beta_1$ subunit in an untreated 10 day old CAM preparation as detected by immunofluorescence immunoreactivity with CSAT, an anti-$\beta_1$ antibody. FIG. 5B shows the distribution of the $\alpha_v\beta_3$ receptor in an untreated 10 day old CAM preparation as detected by immunofluorescence immunoreactivity with LM609, an anti-$\alpha_v\beta_3$ antibody. FIG. 5C shows the distribution of the $\alpha_v\beta_3$ receptor in an βFGF treated 10 day old CAM preparation as detected by immunofluorescence immunoreactivity with LM609, an anti-$\alpha_v\beta_3$ antibody. The treatments and results are described in Example 5C.

FIG. 8A shows an untreated CAM preparation that is devoid of blood vessels. FIG. 8B shows the infiltration of new vasculature into an area previously devoid of vasculature induced by βFGF treatment. FIGS. 8C, 8D and 8E respectively show the effects of antibodies against $\beta_1$ (anti-$\beta_1$; CSAT), $\alpha_v\beta_5$ (anti-$\alpha_v$B %; P3G2) and $\alpha_v\beta_3$ (anti-$\alpha_v\beta_3$; LM609).

FIG. 9A shows the lack of inhibitory effect of intravenous treatment with a control peptide (control peptide tumor) on angiogenesis resulting from tumor induction. The inhibition of such angiogenesis by intravenous injection of peptide 66203 (cyclic RGD tumor) is shown in FIG. 9B. The lack of inhibitory effects or cytotoxicity on mature preexisting vessels following intravenous infusion of peptide 66203 in an are a adjacent to the tumor-treated area is shown in FIG. 9C (cyclic RGD adjacent CAM).

FIGS. 10A-10C illustrate the effect of intravenous application of monoclonal antibodies to growth factor induced angiogenesis as described in Example 7B1). FIG. 10A shows βFGF-induced angiogenesis not exposed to antibody treatment (control). No inhibition of angiogenesis resulted when a similar preparation was treated with anti-$\alpha_v\beta_5$ antibody P3G2 as shown in FIG. 10B. Inhibition of angiogenesis resulted with treatment of anti-$\alpha_v\beta_3$ antibody LM609 as shown in FIG. 10C.

DETAILED DESCRIPTION OF THE INVENTION

A. Definitions

Figures 1A, 1B, 1C, 1D:
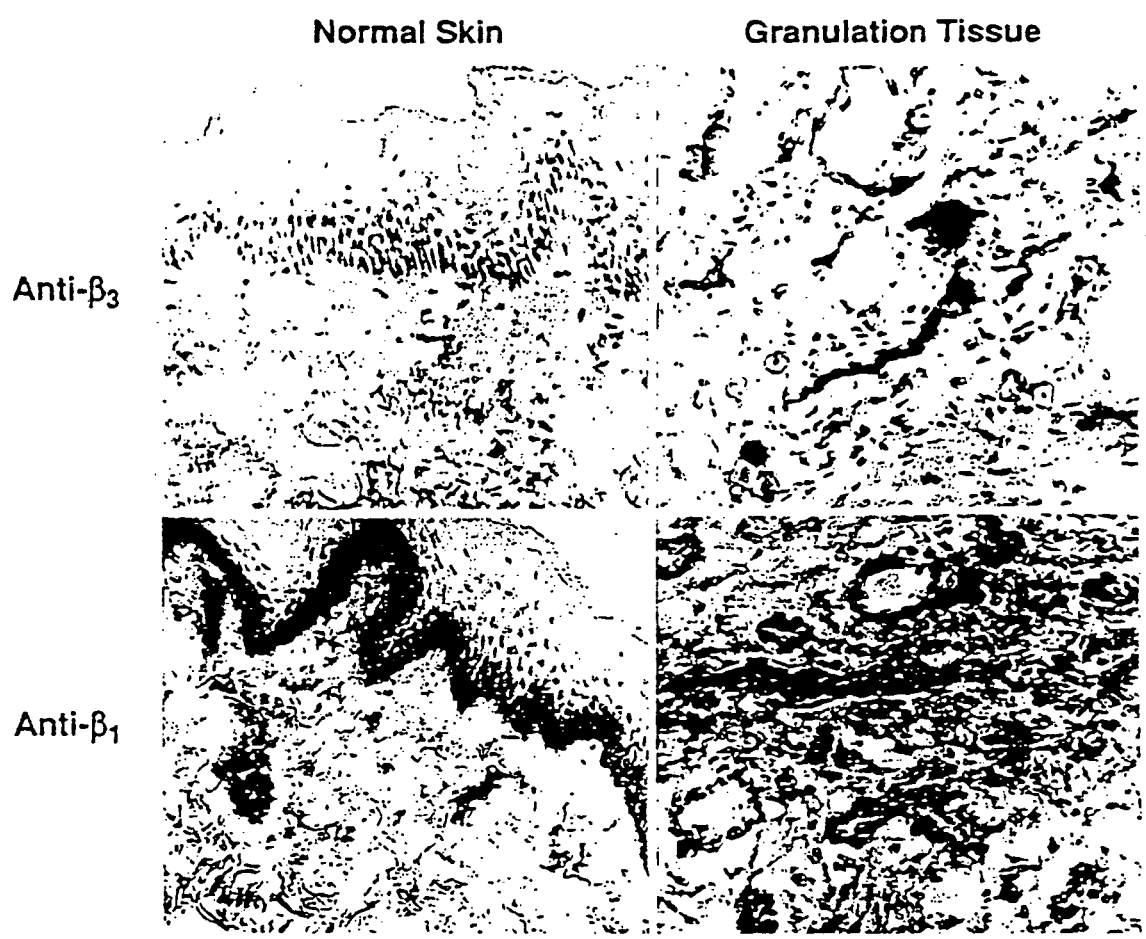
FIGS. 1A-1D illustrate the tissue distribution of the integrin subunits, $\beta_3$, and $\beta_1$, in normal skin and in skin undergoing wound healing designated as granulation tissue. Immunohistochemistry, with antibodies to $\beta_3$ and $\beta_1$ was performed as described in Example 3A.
Figure 3A:
FIGS. 3A-3D illustrate the tissue distribution of the vitronectin integrin receptor, $\alpha_v\beta_3$, in tissue biopsies of bladder cancer, colon cancer, breast cancer and lung cancer, respectively. Immunohistochemistry with the LM609 antibody against $\alpha_v\beta_3$ was performed as described in Example 3C.
Figure 3B:
Figure 3C:
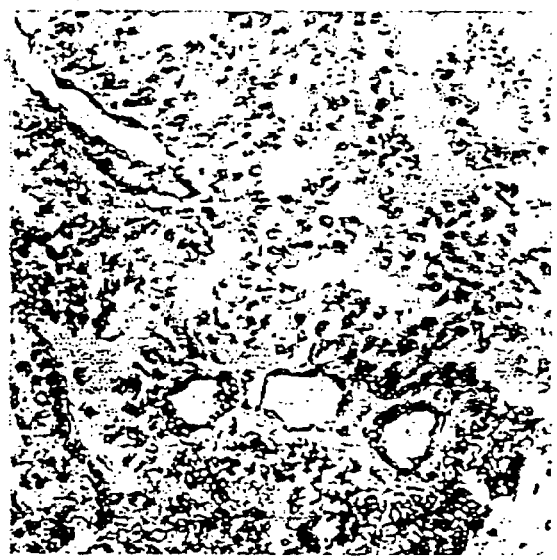
Figure 3D:
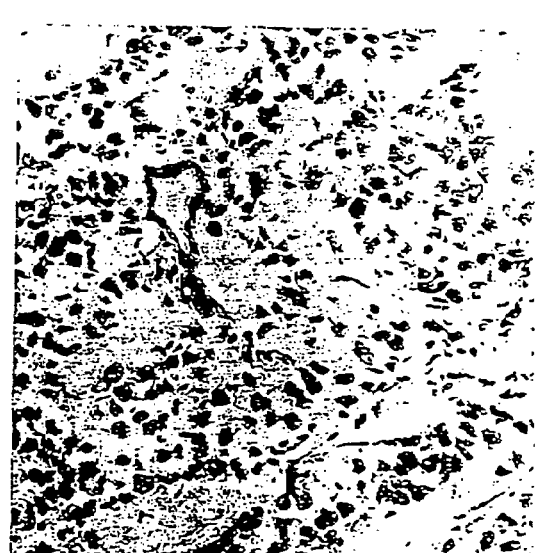

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552-59 (1969) and adopted at 37 CFR §1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

In addition the following have the meanings below:

| | |
|---|---|
| BOC | tert-butyloxycarbonyl |
| DCCI | dicylcohexylcarbodiimide |
| DMF | dimethylformamide |
| OMe | methoxy |
| HOBt | 1-hydroxybezotriazole |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Cyclic peptide: is derived from a corresponding linear peptide and; refers to a peptide in which no free N- or C-termini exist and; and of which the corresponding linear peptide's N-termini forms an amide bond to the C-terminal carboxylate of the said corresponding linear peptide.

Protein: refers to a linear series of greater than 50 amino acid residues connected one to the other as in a polypeptide.

Synthetic peptide: refers to a chemically produced chain of amino acid residues linked together by peptide bonds that is free of naturally occurring proteins and fragments thereof.

B. General Considerations

The present invention relates generally to the discovery that angiogenesis is mediated by the specific vitronectin receptor $\alpha_v\beta_3$, and that inhibition of $\alpha_v\beta_3$ function inhibits angiogenesis. This discovery is important because of the role that angiogenesis plays in a variety of disease processes. By inhibiting angiogenesis, one can intervene in the disease, ameliorate the symptoms, and in some cases cure the disease.

Where the growth of new blood vessels is the cause of, or contributes to, the pathology associated with a disease, inhibition of angiogenesis will reduce the deleterious effects of the disease. Examples include rheumatoid arthritis, diabetic retinopathy, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, only new vessel growth contains substantial $\alpha_v\beta_3$, and therefore the therapeutic methods do not adversely effect mature vessels. Furthermore, $\alpha_v\beta_3$ is not widely distributed in normal tissues, but rather is found selectively on new vessels, thereby assuring that the therapy can be selectively targeted.

The discovery that inhibition of $\alpha_v\beta_3$ alone will effectively inhibit angiogenesis allows for the development of therapeutic compositions with potentially high specificity, and therefore relatively low toxicity. Thus although the invention discloses the use of RGD-peptide-based reagents which have the ability to inhibit one or more integrins, one can design reagents which selectively inhibit $\alpha_v\beta_3$, and therefore do not have the side effect of inhibiting other biological processes other that those mediated by $\alpha_v\beta_3$.

As shown by the present teachings, it is possible to prepare monoclonal antibodies highly selective for immunoreaction with $\alpha_v\beta_3$ that are similarly selective for inhibition of $\alpha_v\beta_3$ function. In addition, RGD-containing peptides can be designed to be selective for inhibition of $\alpha_v\beta_3$, as described further herein.

Prior to the discoveries of the present invention, it was not known that angiogenesis could be inhibited in vivo by the use of reagents that antagonize the biological function of $\alpha_v\beta_3$.

C. Methods for Inhibition of Angiogenesis

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of an $\alpha_v\beta_3$ antagonist.

As described earlier, angiogenesis includes a variety of processes involving neovascularization of a tissue including "sprouting", vasculogenesis, or vessel enlargement, all of which angiogenesis processes are mediated by and dependent upon the expression of $\alpha_v\beta_3$. With the exception of traumatic wound healing, corpus leuteum formation and embryogenesis, it is believed that the majority of angiogenesis processes are associated with disease processes.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Karposi sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as are described in the Examples for detecting $\alpha_v\beta_3$-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a hemangioma or angiofibroma and the like cancer, and the angiogenesis to be inhibited is tumor tissue angiogenesis where there is neovascularization of a tumor tissue. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis according to the present methods. Similarly, the invention provides a method of inhibiting tumor growth by practicing the angiogenesis-inhibiting methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

The present method for inhibiting angiogenesis in a tissue comprises contacting a tissue in which angiogenesis is occurring, or is at risk for occurring, with a composition comprising a therapeutically effective amount of an $\alpha_v\beta_3$ antagonist capable of inhibiting $\alpha_v\beta_3$ binding to its natural ligand. Thus the method comprises administering to a patient a therapeutically effective amount of a physiologically tolerable composition containing an $\alpha_v\beta_3$ antagonist of the invention.

The dosage ranges for the administration of the $\alpha_v\beta_3$ antagonist depend upon the form of the antagonist, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective amount is an amount of $\alpha_v\beta_3$ antagonist sufficient to produce a measurable inhibition of angiogenesis in the tissue being treated, ie., and angiogenesis-inhibiting amount. Inhibition of angiogenesis can be measured in situ by immunohistochemistry, as described herein, or by other methods known to one skilled in the art.

Insofar as an $\alpha_v\beta_3$ antagonist can take the form of $\alpha_v\beta_3$ mimetic, and RGD-containing peptide, an anti-$\alpha_v\beta_3$ monoclonal antibody, or fragment thereof, it is to be appreciated that the potency, and therefore an expression of a "therapeutically effective" amount can vary. However, as shown by the present assay methods, one skilled in the art can readily assess the potency of a candidate $\alpha_v\beta_3$ antagonist of this invention.

Potency of an $\alpha_v\beta_3$ antagonist can be measured by a variety of means including inhibition of angiogenesis in the CAM assay described herein, inhibition of binding of natural ligand to $\alpha_v\beta_3$ as described herein, and the like assays.

A preferred $\alpha_v\beta_3$ antagonist has the ability to substantially inhibit binding of a natural ligand such as fibrinogen or vitronectin to $\alpha_v\beta_3$ in solution at antagonist concentrations of less than 0.5 micromolar (uM), preferably less than 0.1 uM, and more preferably less than 0.05 uM. By "substantially" is meant that at least a 50 percent reduction in binding of fibrinogen is observed by inhibition in the presence of the $\alpha_v\beta_3$ antagonist, and at 50% inhibition is referred to herein as an $IC_{50}$ value.

A more preferred $\alpha_v\beta_3$ antagonist exhibits selectivity for $\alpha_v\beta_3$ over other integrins. Thus, a preferred $\alpha_v\beta_3$ antagonist substantially inhibits fibrinogen binding to $\alpha_v\beta_3$ but does not substantially inhibit binding of fibrinogen to another integrin, such as $\alpha_v\beta_1$, $\alpha_v\beta_5$ or $\alpha_{IIb}\beta_3$. Particularly preferred is an $\alpha_v\beta_3$ antagonist that exhibits a 10-fold to 100-fold lower $IC_{50}$ activity at inhibiting fibrinogen binding to $\alpha_v\beta_3$ compared to the $IC_{50}$ activity at inhibiting fibrinogen binding to another integrin. Exemplary assays for measuring $IC_{50}$ activity at inhibiting fibrinogen binding to an integrin are described in the Examples.

A therapeutically effective amount of an $\alpha_v\beta_3$ antagonist of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

A therapeutically effective amount of an $\alpha_v\beta_3$ antagonist of this invention in the form of a polypeptide is typically an amount of polypeptide such that when administered in a physiologically tolerable composition is sufficient to achieve a plasma concentration of from about 0.1 microgram (ug) per milliliter (ml) to about 200 ug/ml, preferably from about 1 ug/ml to about 150 ug/ml. Based on a polypeptide having a mass of about 500 grams per mole, the preferred plasma concentration in molarity is from about 2 micromolar (uM) to about 5 millimolar (mM) and preferably about 100 uM to 1 mM polypeptide antagonist. Stated differently, the dosage per body weight can vary from about 0.1 mg/kg to about 300 mg/kg, and preferably from about 0.2 mg/kg to about 200 mg/kg, in one or more dose administrations daily, for one or several days.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intracavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

D. Therapeutic Compositions

The present invention contemplates therapeutic compositions useful for practicing the therapeutic methods described herein. Therapeutic compositions of the present invention contain a physiologically tolerable carrier together with an $\alpha_v\beta_3$ antagonist as described herein, dissolved or dispersed therein as an active ingredient. In a preferred embodiment, the therapeutic $\alpha_v\beta_3$ antagonist composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Particularly preferred are the salts of TFA and HCl, when used in the preparation of cyclic polypeptide $\alpha_v\beta_3$ antagonists. Representative salts of peptides are described in the Examples.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an $\alpha_v\beta_3$ antagonist of the present invention, typically formulated to contain an amount of at least 0.1 weight percent of antagonist per weight of total therapeutic composition. A weight percent is a ratio by weight of inhibitor to total composition. Thus, for example, 0.1 weight percent is 0.1 grams of inhibitor per 100 grams of total composition.

E. Antagonists of Integrin $\alpha_v\beta_3$ $\alpha_v\beta_3$ antagonists are used in the present methods for inhibiting angiogenesis in tissues, and can take a variety of forms that include compounds which interact with $\alpha_v\beta_3$ in a manner such that functional interactions with natural $\alpha_v\beta_3$ ligands are interfered. Exemplary antagonists include analogs of $\alpha_v\beta_3$ derived from the ligand binding site on $\alpha_v\beta_3$, mimetics of either $\alpha_v\beta_3$ or a natural ligand of $\alpha_v\beta_3$ that mimic the structural region involved in $\alpha_v\beta_3$-ligand binding interactions, polypeptides having a sequence corresponding to the RGD-containing domain of a natural ligand of $\alpha_v\beta_3$, and antibodies which immunoreact with either $\alpha_v\beta_3$ or the natural ligand, all of which exhibit antagonist activity as defined herein.

1. Polypeptides

In one embodiment, the invention contemplates $\alpha_v\beta_3$ antagonists in the form of polypeptides. A polypeptide (peptide) $\alpha_v\beta_3$ antagonist can have the sequence characteristics of either the natural ligand of $\alpha_v\beta_3$ or $\alpha_v\beta_3$ itself at the region involved in $\alpha_v\beta_3$-ligand interaction and exhibits $\alpha_v\beta_3$ antagonist activity as described herein. A preferred $\alpha_v\beta_3$ antagonist peptide contains the RGD tripeptide and corresponds in sequence to the natural ligand in the RGD-containing region.

Preferred RGD-containing polypeptides have a sequence corresponding to the amino acid residue sequence of the RGD-containing region of a natural ligand of $\alpha_v\beta_3$ such as fibrinogen, vitronectin, von Willebrand factor, laminin, thrombospondin, and the like ligands. The sequence of these $\alpha_v\beta_3$ ligands are well known. Thus, an $\alpha_v\beta_3$ antagonist peptide can be derived from any of the natural ligands, although fibrinogen and vitronectin are preferred.

A particularly preferred $\alpha_v\beta_3$ antagonist peptide preferentially inhibits $\alpha_v\beta_3$ binding to its natural ligand(s) when compared to other integrins, as described earlier. These $\alpha_v\beta_3$-specific peptides are particularly preferred at least because the specificity for $\alpha_v\beta_3$ reduces the incidence of undesirable side effects such as inhibition of other integrins. The identification of preferred $\alpha_v\beta_3$ antagonist peptides having selectivity for $\alpha_v\beta_3$ can readily be identified in a typical inhibition of binding assay, such as the ELISA assay described in the Examples.

In one embodiment, a polypeptide of the present invention comprises no more than about 100 amino acid residues, preferably no more than about 60 residues, more preferably no more than about 30 residues. Peptides can be linear or cyclic, although particularly preferred peptides are cyclic.

Preferred cyclic and linear peptides and their designations are shown in Table 1 in the Examples.

It should be understood that a subject polypeptide need not be identical to the amino acid residue sequence of a $\alpha_v\beta_3$ natural ligand, so long as it includes the required sequence and is able to function as an $\alpha_v\beta_3$ antagonist in an assay such as is described herein.

A subject polypeptide includes any analog, fragment or chemical derivative of a polypeptide whose amino acid residue sequence is shown herein so long as the polypeptide is an $\alpha_v\beta_3$ antagonist. Therefore, a present polypeptide can be subject to various changes, substitutions, insertions, and deletions where such changes provide for certain advantages in its use. In this regard, $\alpha_v\beta_3$ antagonist polypeptide of this invention corresponds to, rather than is identical to, the sequence of a recited peptide where one or more changes are made and it retains the ability to function as an $\alpha_v\beta_3$ antagonist in one or more of the assays as defined herein.

Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence specifically shown herein in which one or more residues have been conservatively substituted with a functionally similar residue and which displays the $\alpha_v\beta_3$ antagonist activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of an $\alpha_v\beta_3$ natural ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier.

Labels, solid matrices and carriers that can be used with the polypeptides of this invention are described hereinbelow.

Amino acid residue linkers are usually at least one residue and can be 40 or more residues, more often 1 to 10 residues, but do not form $\alpha_v\beta_3$ ligand epitopes. Typical amino acid residues used for linking are tyrosine, cysteine, lysine, glutamic and aspartic acid, or the like. In addition, a subject polypeptide can differ, unless otherwise specified, from the natural sequence of an $\alpha_v\beta_3$ ligand by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of forming salts with the peptides of the present invention include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A peptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W.H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., Int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al., Peptides 1992, pp. 393-394, ESCOM Science Publishers, B. V., 1993. Typically, tertbutoxycarbonyl protected peptide methyl ester is dissolved in methanol and sodium hydroxide solution are added and the admixture is reacted at 20° C. (20 C) to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted in to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

A particularly preferred cyclic peptide synthesis method is described by Gurrath et al., *Eur. J. Biochem.*, 210:911-921 (1992), and described in the Examples. Particularly preferred peptides for use in the present methods are c-(GrGDFV) (SEQ ID NO 4), c-(RGDfV) (SEQ ID NO 5), c-(RADfV) (SEQ ID NO 6), c-(RGDFv) (SEQ ID NO 7) and linear peptide YTAECKPQVTRGDVF (SEQ ID NO 8), where "c-" indicates a cyclic peptide, the upper case letters are single letter code for an L-amino acid and the lower case letters are single letter code for D-amino acid. The amino acid residues sequence of these peptides are also shown in SEQ. ID NOs 4, 5, 6, 7 and 8, respectively.

2. Monoclonal Antibodies

The present invention describes, in one embodiment, $\alpha_v\beta_3$ antagonists in the form of monoclonal antibodies which immunoreact with $\alpha_v\beta_3$ and inhibit $\alpha_v\beta_3$ binding to its natural ligand as described herein. The invention also describes cell lines which produce the antibodies, methods for producing the cell lines, and methods for producing the monoclonal antibodies.

A monoclonal antibody of this invention comprises antibody molecules that 1) immunoreact with isolated $\alpha_v\beta_3$ and 2) inhibit fibrinogen binding to $\alpha_v\beta_3$. Preferred monoclonal antibodies which preferentially bind to $\alpha_v\beta_3$ include a monoclonal antibody having the immunoreaction characteristics of Mab LM609, secreted by hybridoma cell line ATCC™ HB 9537. The hybridoma cell line ATCC™ HB 9537 was deposited pursuant to Budapest Treaty requirements with the American Type Culture Collection (ATCC™), 1081 University Boulevard, Manassas, Va. 20110-2209, USA, on Sep. 15, 1987.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules and those portions of an immunoglobulin molecule that contain the paratope, including those portions known in the art as Fab, Fab', F(ab')$_2$ and F(v), and also referred to as antibody fragments.

In another preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

For example, Fab and F(ab')$_2$ portions (fragments) of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact immunoglobulin molecules are preferred, and are utilized as illustrative herein.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495-497 (1975), which description is incorporated by reference. Additional methods are described by Zola, *Monoclonal Antibodies: A Manual of Techniques*, CRC Press, Inc. (1987). The hybridoma supernates so prepared can be screened for the presence of antibody molecules that immunoreact with $\alpha_v\beta_3$ and for inhibition of $\alpha_v\beta_3$ binding to natural ligands.

Briefly, to form the hybridoma from which the monoclonal antibody composition is produced, a myeloma or other self-perpetuating cell line is fused with lymphocytes obtained from the spleen of a mammal hyperimmunized with a source of $\alpha_v\beta_3$, such as $\alpha_v\beta_3$ isolated from M21 human melanoma cells as described by Cheresh et al., *J. Biol. Chem.*, 262:17703-17711 (1987).

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/i glucose, 20 mM glutamine, and 20% fetal calf serum. An exemplary inbred mouse strain is the BALB/c strain.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728-5732 (1989); and Huse et al., *Science*, 246:1275-1281 (1989).

Also contemplated by this invention is the hybridoma cell, and cultures containing a hybridoma cell that produce a monoclonal antibody of this invention. Particularly preferred is the hybridoma cell line that secretes monoclonal antibody Mab LM609 designated ATCC™ HB 9537. Mab LM609 was prepared as described by Cheresh et al., J. Biol. Chem., 262:17703-17711 (1987), and its preparation is also described in the Examples.

The invention contemplates, in one embodiment, a monoclonal antibody that has the immunoreaction characteristics of Mab LM609.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides is well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Use of the term "having the binding specificity of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

Thus, the invention contemplates, in one embodiment, a monoclonal antibody of this invention that is humanized by grafting to introduce components of the human immune system without substantially interfering with the ability of the antibody to bind antigen.

F. Methods for Identifying Antagonists of $\alpha_v\beta_3$

The invention also described assay methods for identifying candidate $\alpha_v\beta_3$ antagonists for use according to the present methods. In these assay methods candidate molecules are evaluated for their potency in inhibiting $\alpha_v\beta_3$ binding to natural ligands, and furthermore are evaluated for their potency in inhibiting angiogenesis in a tissue.

The first assay measures inhibition of direct binding of natural ligand to $\alpha_v\beta_3$, and a preferred embodiment is described in detail in the Examples. The assay typically measures the degree of inhibition of binding of a natural ligand, such as fibrinogen, to isolated $\alpha_v\beta_3$ in the solid phase by ELISA.

The assay can also be used to identify compounds which exhibit specificity for $\alpha_v\beta_3$ and do not inhibit natural ligands from binding other integrins. The specificity assay is conducted by running parallel ELISA assays where both $\alpha_v\beta_3$ and other integrins are screened concurrently in separate assay chambers for their respective abilities to bind a natural ligand and for the candidate compound to inhibit the respective abilities of the integrins to bind a preselected ligand. Preferred screening assay formats are described in the Examples.

The second assay measures angiogenesis in the chick chorioallantoic membrane (CAM) and is referred to as the CAM assay. The CAM assay has be described in detail by others, and further has been used to measure both angiogenesis and neovascularization of tumor tissues. See Ausprunk et al., *Am. J. Pathol.*, 79:597-618 (1975) and Ossonski et al., *Cancer Res.*, 40:2300-2309 (1980).

The CAM assay is a well recognized assay model for in vivo angiogenesis because neovascularization of whole tissue is occurring, and actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Synthetic Peptides

The linear and cyclic polypeptides listed in Table 1 were synthesized using standard solid-phase synthesis techniques as, for example, described by Merrifield, *Adv. Enzymol.*, 32:221-96, (1969), and Fields, G. B. and Noble, R. L., *Int. J. Peptide Protein Res.*, 35:161-214, (1990).

Two grams (g) of BOC-Gly-D-Arg-Gly-Asp-Phe-Val-OMe (SEQ ID NO 1) were first dissolved in 60 milliliters (ml) of methanol to which was added 1.5 ml of 2 N sodium hydroxide solution to form an admixture. The admixture was then stirred for 3 hours at 20 degress C. (20 C). After evaporation, the residue was taken up in water, acidified to pH 3 with diluted HCl and extracted with ethyl acetate. The extract was dried over $Na_2SO_4$, evaporated again and the resultant BOC-Gly-D-Arg-Gly-Asp-Phe-Val-OH (SEQ ID NO 2) was stirred at 20 C for 2 hours with 20 ml of 2 N HCl in dioxane. The resultant admixture was evaporated to obtain H-Gly-D-Arg-Gly-Asp-Phe-Val-OH (SEQ ID NO 3) that was subsequently dissolved in a mixture of 1800 ml of dichloromethane and 200 ml of dimethylformamide (DMF) followed by cooling to 0 C. Thereafter, 0.5 g of dicyclohexylcarbodiimide (DCCI), 0.3 g of 1-hydroxybenzotriazole (HOBt) and 0.23 ml of N-methylmorpholine were added successively with stirring.

The resultant admixture was stirred for a further 24 hours at 0 C and then at 20 C for another 48 hours. The solution was concentrated and treated with a mixed bed ion exchanger to free it from salts. After the resulting resin was removed by filtration, the clarified solution was evaporated and the residue was purified by chromatography resulting in the recovery of cyclo(-Gly-D-Arg-Gly-Asp-Phe-Val) (SEQ ID NO 4). The following peptides, listed in Table 1 using single letter code amino acid residue abbreviations and identified by a peptide number designation, were obtained analogously: cyclo(Arg-Gly-Asp-D-Phe-Val) (SEQ ID NO 5); cyclo(Arg-Ala-Asp-D-Phe-Val) (SEQ ID NO 6); cyclo (Arg-D-Ala-Asp-Phe-Val) (SEQ ID NO 9); cyclo(Arg-Gly-Asp-Phe-D-Val) (SEQ ID NO 7). A peptide designated as 66203, having an identical sequence to that of peptide 62184, only differed from the latter by containing the salt HCl rather than the TFA salt present in 62184. In inhibition of angiogenesis assays as described in Example 7 where the synthetic peptides were used, the 66203 peptide having HCl was slightly more effective in inhibiting angiogenesis than the identical peptide in TFA.

TABLE 1

| Peptide No. | Amino Acid Sequence | SEQ ID NO |
|---|---|---|
| 62181 | cyclo (GrGDFV) | 4 |
| 62184 | cyclo (RGDfV) | 5 |
| 62185 | cyclo (RADfV) | 6 |
| 62187 | cyclo (RGDFv) | 7 |
| 62880 | YTAECKPQVTRGDVF | 8 |
| 62186 | cyclo (RaDFV) | 9 |
| 62175 | cyclo (ARGDfL) | 10 |
| 62179 | cyclo (GRGDfL) | 11 |
| 62411 | TRQVVCDLGNPM | 12 |
| 62503 | GVVRNNEALARLS | 13 |
| 62502 | TDVNGDGRHDL | 14 |

* Lower case letters indicate a D-amino acid; capital letters indicate a L-amino acid.

2. Monoclonal Antibodies

The monoclonal antibody LM609 secreted by hybridoma ATCC™ HB 9537 was produced using standard hybridoma methods by immunization with isolated $\alpha_v\beta_3$ adsorbed onto Sepharose-lentil lectin beads. The $\alpha_v\beta_3$ had been isolated from human melanoma cells designated M21, and antibody was produced as described by Cheresh et al., J. Biol. Chem., 262:17703-17711 (1987). M21 cells were provided by Dr. D. L. Morton (University of California at Los Angeles, Calif.) and grown in suspension cultures in RPMI 1640 culture medium containing 2 mM L-glutamine, 50 mg/ml gentamicin sulfate and 10% fetal calf serum.

Monoclonal antibody LM609 has been shown to immunoreact with $\alpha_v\beta_3$ complex, and not immunoreact with $\alpha_v$ subunit, with $\beta_3$ subunit, or with other integrins.

3. Characterization of the Tissue Distribution of $\alpha_v\beta_3$ Expression

A. Immunofluorescence with Anti-Integrin Receptor Antibodies

During wound healing, the basement membranes of blood vessels express several adhesive proteins, including von Willebrand factor, fibronectin, and fibrin. In addition, several members of the integrin family of adhesion receptors are expressed on the surface of cultured smooth muscle and endothelial cells. See, Cheresh, Proc. Natl. Acad. Sci., USA, 84:6471 (1987); Janat et al., J. Cell Physiol., 151:588 (1992); and Cheng et al., J. Cell Physiol., 139:275 (1989). Among these integrins is $\alpha_v\beta_3$, the endothelial cell receptor for von Willebrand factor, fibrinogen (fibrin), and fibronectin as described by Cheresh, Proc. Natl. Acad. Sci. USA, 84:6471 (1987). This integrin initiates a calcium-dependent signaling pathway leading to endothelial cell migration, and therefore appears to play a fundamental role in vascular cell biology as described by Leavelsey et al., J. Cell Biol., 121:163 (1993).

To investigate the expression of $\alpha_v\beta_3$ during angiogenesis, human wound granulation tissue or adjacent normal skin was obtained from consenting patients, washed with 1 ml of phosphate buffered saline and embedded in O.T.C medium (Tissue Tek). The embedded tissues were snap frozen in liquid nitrogen for approximately 30 to 45 seconds. Six micron thick sections were cut from the frozen blocks on a cryostat microtome for subsequent immunoperoxidase staining with antibodies specific for either $\beta_3$ integrins ($\alpha_v\beta_3$ or $\alpha_{IIb}\beta_3$) or the $\beta_1$ subfamily of integrins.

The results of the staining of normal human skin and wound granulation tissue are shown in FIGS. 1A-1D. Monoclonal antibodies AP3 and LM534, directed to $\beta_3$ and $\beta_1$ integrins, respectively, were used for immunohistochemical analysis of frozen sections. Experiments with tissue from four different human donors yielded identical results. The photomicrographs are shown at magnification of 300×.

The $\alpha_v\beta_3$ integrin was abundantly expressed on blood vessels in granulation tissue (FIG. 1B) but was not detectable in the dermis and epithelium of normal skin from the same donor (FIG. 1A). In contrast, $\beta_1$ integrins were abundantly expressed on blood vessels and stromal cells in both normal skin (FIG. 1C) and granulation tissue (FIG. 1D) and, as previously shown as described by Adams et al., Cell, 63:425 (1991), on the basal cells within the epithelium.

B. Immunofluorescence with Anti-Ligand Antibodies

Additional sections of the human normal skin and granulation tissues prepared above were also examined for the presence of the ligands for the $\beta_3$ and $\beta_1$ integrins, von Willebrand factor and laminin, respectively., Von Willebrand factor localized to the blood vessels in normal skin (FIG. 2A) and granulation tissue (FIG. 2B), whereas laminin localized to all blood vessels as well as the epithelial basement membrane in both tissue preparations (FIGS. 2C and 2D).

C. Distribution Anti-$\alpha_v\beta_3$ Antibodies on Cancer Tissue

In addition to the above analyses, biopsies of cancer tissue from human patients were also examined for the presence and distribution of $\alpha_v\beta_3$. The tissues were prepared as described Example 1A with the exception that they were stained with monoclonal antibody LM609 prepared in Example 2 that is specific for the integrin receptor complex, $\alpha_v\beta_3$. In addition, tumors were also prepared for microscopic histological analysis by fixing representative examples of tumors in Bulins Fixative for 8 hours and serial sections cut and H&E stained.

The results of immunoperoxidase staining of bladder, colon breast and lung cancer tissues are shown in FIGS. 3A-3D, respectively. $\alpha_v\beta_3$ is abundantly expressed only on the blood vessels present in the four cancer biopsies analyzed and not on any other cells present in the tissue.

The results described herein thus show that the $\alpha_v\beta_3$ integrin receptor is selectively expressed in specific tissue types, namely granulated, metastatic tissues and other tissues in which angiogenesis is occurring and not normal tissue where the formation of new blood vessels has stopped. These tissues therefore provide an ideal target for therapeutic aspects of this invention.

4. Identification of $\alpha_v\beta_3$-Specific Synthetic Peptides Detected by a Ligand-Receptor Binding Assay The synthetic peptides prepared in Example 1 were screened by measuring their ability to antagonize $\alpha_v\beta_3$ and $\alpha_{IIb}\beta_3$ receptor binding activity in purified ligand-receptor binding assays. The method for these binding studies has been described by Barbas et al., *Proc. Natl. Acad. Sci., USA*, 90:10003-10007 (1993) and Smith et al., *J. Biol. Chem.*, 265:11008-11013 (1990), the disclosures of which are hereby incorporated by reference.

Briefly, selected purified integrins were separately immobilized in Titertek microtiter wells at a coating concentration of 50 nanograms (ng) per well. The purification of the receptors used in the ligand-receptor binding assays are well known in the art and are readily obtainable with methods familiar to one of ordinary skill in the art. After incubation for 18 hours at 4 C, nonspecific binding sites on the plate were blocked with 10 milligrams/milliliter (mg/ml) of bovine serum albumin (BSA) in Tris-buffered saline. For inhibition studies, various concentrations of selected peptides from Table 1 were tested for the ability to block the binding of $^{125}$I-vitronectin or $^{125}$I-fibrinogen to the integrin receptors, $\alpha_v\beta_3$ and $\alpha_{IIb}\beta_3$. Although these ligands exhibit optimal binding for a particular integrin, vitronectin for $\alpha_v\beta_3$ and fibrinogen for $\alpha_{IIb}\beta_3$, inhibition of binding studies using peptides to block the binding of fibrinogen to either receptor allowed for the accurate determination of the amount in micromoles (uM) of peptide necessary to half-maximally inhibit the binding of receptor to ligand. Radiolabeled ligands were used at concentrations of 1 nM and binding was challenged separately with unlabeled synthetic peptides.

Following a three hour incubation, free ligand was removed by washing and bound ligand was detected by gamma counting. The data from the assays where selected cyclic peptides listed in Table 1 were used to inhibit the binding of receptors and radiolabeled fibrinogen to separately immobilized $\alpha_v\beta_3$ and $\alpha_{IIb}\beta_3$ receptors were highly reproducible with the error between data points typically below 11%. The IC$_{50}$ data in micromoles (IC$_{50}$ uM) are expressed as the average of duplicate data points ± the standard deviation as shown in Table 2.

TABLE 2

| Peptide No. | $\alpha_v\beta_3$ (IC$_{50}$ uM) | $\alpha_{IIb}\beta_3$ (IC$_{50}$ uM) |
|---|---|---|
| 62181 | 1.96 ± 0.62 | 14.95 ± 7.84 |
| 62184 | 0.05 ± 0.001 | 0.525 ± 0.10 |
| 62185 | 0.885 ± 0.16 | 100 ± 0.001 |
| 62187 | 0.05 ± 0.001 | 0.26 ± 0.056 |
| 62186 | 57.45 ± 7.84 | 100 ± 0.001 |
| 62175 | 1.05 ± 0.07 | 0.63 ± 0.18 |
| 62179 | 0.395 ± .21 | 0.055 ± 0.007 |

Thus, the RGD-containing or RGD-derivatized cyclized peptides 62181, 62184, 62185 and 62187, each having one D-amino acid residue, exhibited preferential inhibition of fibrinogen binding to the $\alpha_v\beta_3$ receptor as measured by the lower concentration of peptide required for half-maximal inhibition as compared to that for the $\alpha_{IIb}\beta_3$ receptor. In contrast, the other RGD-containing or RGD-derivatized cyclic peptides, 62186, 62175 and 62179, were not as effective in blocking fibrinogen binding to $\alpha_v\beta_{31}$ with the latter two peptides exhibiting preferential inhibition of fibrinogen binding to $\alpha_{IIb}\beta_3$ as compared to $\alpha_v\beta_3$.

Similar inhibition of binding assays were performed with linearized peptides having or lacking an RGD motif, the sequences of which were derived from the $\alpha_v$ receptor subunit, $\alpha_{IIb}$ receptor subunit or vitronectin ligand amino acid residue sequences. The sequences of the linear peptides, 62880 (VN-derived amino acid residues 35-49), 62411 ($\alpha_v$-derived amino acid residues 676-687); 62503 ($\alpha_v$-derived amino acid residues 655-667) and 62502 ($\alpha_{IIb}$-derived amino acid residues 296-306), are listed in Table 1. Each of these peptides were used in separate assays to inhibit the binding of either vitronectin (VN) or fibrinogen (FG) to either $\alpha_{IIb}\beta_3$ or $\alpha_v\beta_3$. The IC$_{50}$ data in micromoles (IC$_{50}$ uM) of an individual assay for each experiment is shown in Table 3.

TABLE 3

| Peptide No. | $\alpha_{IIb}\beta_3$ | | $\alpha_v\beta_3$ | |
|---|---|---|---|---|
| | FG | VN | FG | VN |
| 62880 | 4.2 | 0.98 | <0.1 | 0.5 |
| 62411 | >100 | >100 | >100 | >100 |
| 62503 | >100 | >100 | >100 | >100 |
| 62502 | 90 | 5 | >100 | >100 |

The results of inhibition of ligand binding assays to selected integrin receptors with linearized peptides show that only peptide 62880 was effective at inhibiting the half-maximal binding of either FG or VN to $\alpha_v\beta_3$ as measured by the lower concentration of peptide required for half-maximal inhibition as compared to $\alpha_{IIb}\beta_3$ receptor. None of the other linearized peptides were effective at blocking ligand binding to $\alpha_v\beta_3$ although peptide 62502 was effective at blocking VN binding to $\alpha_{IIb}\beta_3$.

Thus, the ligand-receptor assay described herein can be used to screen for both circular or linearized synthetic peptides that exhibit selective specificity for a particular integrin receptor, specifically $\alpha_v\beta_3$, as used as vitronectin receptor ($\alpha_v\beta_3$) antagonists in practicing this invention.

5. Characterization of the Untreated Chick Chorioallantoic Membrane (CAM)

A. Preparation of the CAM

Angiogenesis can be induced on the chick chorioallantoic membrane (CAM) after normal embryonic angiogenesis has resulted in the formation of mature blood vessels. Angiogenesis has been shown to be induced in response to specific cytokines or tumor fragments as described by Leibovich et al., *Nature*, 329:630 (1987) and Ausprunk et al., *Am. J. Pathol.*, 79:597 (1975). CAMs were prepared from chick embryos for subsequent induction of angiogenesis and inhibition thereof as described in Examples 6 and 7, respectively. Ten day old chick embryos were obtained from McIntyre Poultry (Lakeside, Calif.) and incubated at 99.5 degrees Fahrenheit with 60% humidity. A small hole was made through the shell at the end of the egg directly over the air sac with the use of a small crafts drill (Dremel, Division of Emerson Electric Co. Racine Wis.). A second hole was drilled on the broad side of the egg in a region devoid of embryonic blood vessels determined previously by candling the egg. Negative pressure was applied to the original hole, which resulted in the CAM (chorioallantoic membrane) pulling away from the shell membrane and creating a false air sac over the CAM. A 1.0 centimeter (cm)×1.0 cm square window was cut through the shell over the dropped CAM with the use of a small model grinding wheel (Dremel). The small window allowed direct access to the underlying CAM.

The resultant CAM preparation was then either used at 6 days of embryogenesis, a stage marked by active neovascularization, without additional treatment to the CAM reflecting the model used for evaluating effects on embryonic neovascularization or used at 10 days of embryogenesis where angiogenesis has subsided. The latter preparation was thus used in this invention for inducing renewed angiogenesis in response to cytokine treatment or tumor contact as described in Example 6.

B. Histology of the CAM

To analyze the microscopic structure of the chick embryo CAMs and/or human tumors that were resected from the chick embryos as described in Example 8, the CAMs and tumors were prepared for frozen sectioning as described in Example 3A. Six micron thick sections were cut from the frozen blocks on a cryostat microtome for immunofluorescence analysis.

Figure 4:
FIG. 4 illustrates a typical photomicrograph of a CAM of this invention devoid of blood vessels in an untreated 10 day old chick embryo. The preparation is described in Example 5B.

FIG. 4 shows a typical photomicrograph of an area devoid of blood vessels in an untreated 10 day old CAM. As angiogenesis in the CAM system is subsiding by this stage of embryogenesis, the system is useful in this invention for stimulating the production of new vasculature from existing vessels from adjacent areas into areas of the CAM currently lacking any vessels.

C. Integrin Profiles in the CAM Detected by Immunofluorescence

To view the tissue distribution of integrin receptors present in CAM tissues, 6 micron (um) frozen sections of both tumor tissue and chick embryo CAM tissues were fixed in acetone for 30 seconds and stained by immunofluorescence with 10 micrograms/milliliter (ug/ml) mAb CSAT, a monoclonal antibody specific for the $\beta_1$ integrin subunit as described by Buck et al., *J. Cell Biol.*, 107:2351 (1988) and thus used for controls, or LM609 as prepared in Example 2. Primary staining was followed by staining with a 1:250 dilution of goat anti-mouse rodamine labeled secondary antibody (Tango) to allow for the detection of the primary immunoreaction product. The sections were then analyzed with a Zeiss immunofluorescence compound microscope.

Figure 5A:
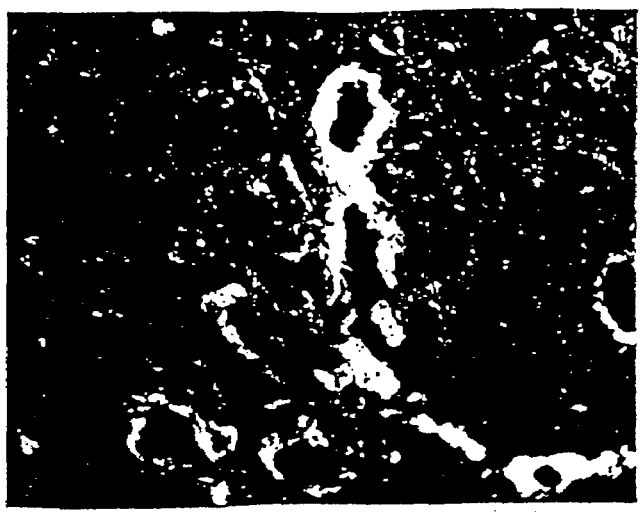
FIGS. 5A-5C illustrate the tissue distribution of the integrins $\beta_1$ and $\alpha_v\beta_3$ in the CAM preparation of this invention.
Figure 5B:

The results of the immunofluorescence analysis show that the mature blood vessels present in an untreated 10 day chick embryo expressed the integrin $\beta_1$ subunit (FIG. 5A). In contrast, in a serial section of the tissue shown in FIG. 5A, no immunoreactivity with LM609 was revealed (FIG. 5B). Thus, the integrin $\alpha_v\beta_3$ detected by the LM609 antibody was not actively being expressed by the mature blood vessels present in a 10 day old untreated chick embryo. As shown in the CAM model and in the following Examples, while the blood vessels are undergoing new growth in normal embryogenesis or induced by either cytokines or tumors, the blood vessels are expressing $\alpha_v\beta_3$. However, following active neovascularization, once the vessels have stopped developing, the expression of $\alpha_v\beta_3$ diminishes to levels not detectable by immunofluorescence analysis. This regulation of $\alpha_v\beta_3$ expression in blood vessels undergoing angiogenesis as contrasted to the lack of expression in mature vessels provides for the unique ability of this invention to control and inhibit angiogenesis as shown in the following Examples as modeled using the CAM angiogenesis assay system.

6. CAM Angiogenesis Assay

A. Angiogenesis Induced by Growth Factors

Angiogenesis has been shown to be induced by cytokines or growth factors as referenced in Example 5A. In the experiments described herein, angiogenesis in the CAM preparation described in Example 5 was induced by growth factors that were topically onto the CAM blood vessels as described herein.

Angiogenesis was induced by placing a 5 millimeter (mm)×5 mm Whatman filter disk (Whatman Filter paper No.1.) saturated with Hanks Balanced Salt Solution (HBSS) or HBSS containing 150 nanograms/milliliter (ng/ml) recombinant basic fibroblast growth factor (OFGF) (Genzyme, Cambridge, Mass.) on the CAM of a 10-day chick embryo in a region devoid of blood vessels and the windows were latter sealed with tape. In other assays, 125 ng/ml OFGF was also effective at inducing blood vessel growth. Angiogenesis was monitored by photomicroscopy after 72 hours. CAMs were snap frozen, and 6 um cryostat sections were fixed with acetone and stained by immunofluorescence as described in Example 5C with 10 ug/ml of either anti-$\beta_1$ monoclonal antibody CSAT or LM609.

Figure 5C:

The immunofluorescence photomicrograph in FIG. 5C shows enhanced expression of $\alpha_v\beta_3$ during $\beta$FGF-induced angiogenesis on the chick CAM in contrast with the absence of $\alpha_v\beta_3$ expression in an untreated chick CAM as shown in FIG. 5B. $\alpha_v\beta_3$ was readily detectable on many (75% to 80%) of the vessels on the $\beta$FGF-treated CAMs. In addition, the expression of integrin $\beta_1$ did not change from that seen in an untreated CAM as $\beta_1$ was also readily detectable on stimulated blood vessels.

The relative expression of $\alpha_v\beta_3$ and $\beta_1$ integrins were then quantified during $\beta$FGF-induced angiogenesis by laser confocal image analysis of the CAM cryostat sections. The stained sections were then analyzed with a Zeiss laser confocal microscope. Twenty-five vessels stained with LM609 and 15 stained with CSAT (average size ~1200 sq mm$^2$, range 350 to 3,500 mm$^2$) were selected from random fields and the average rhodamine fluorescence for each vessel per unit area was measured in arbitrary units by laser confocal image analysis. Data are expressed as the mean fluorescence intensity in arbitrary units of vessels±standard error (SE).

Figure 6:
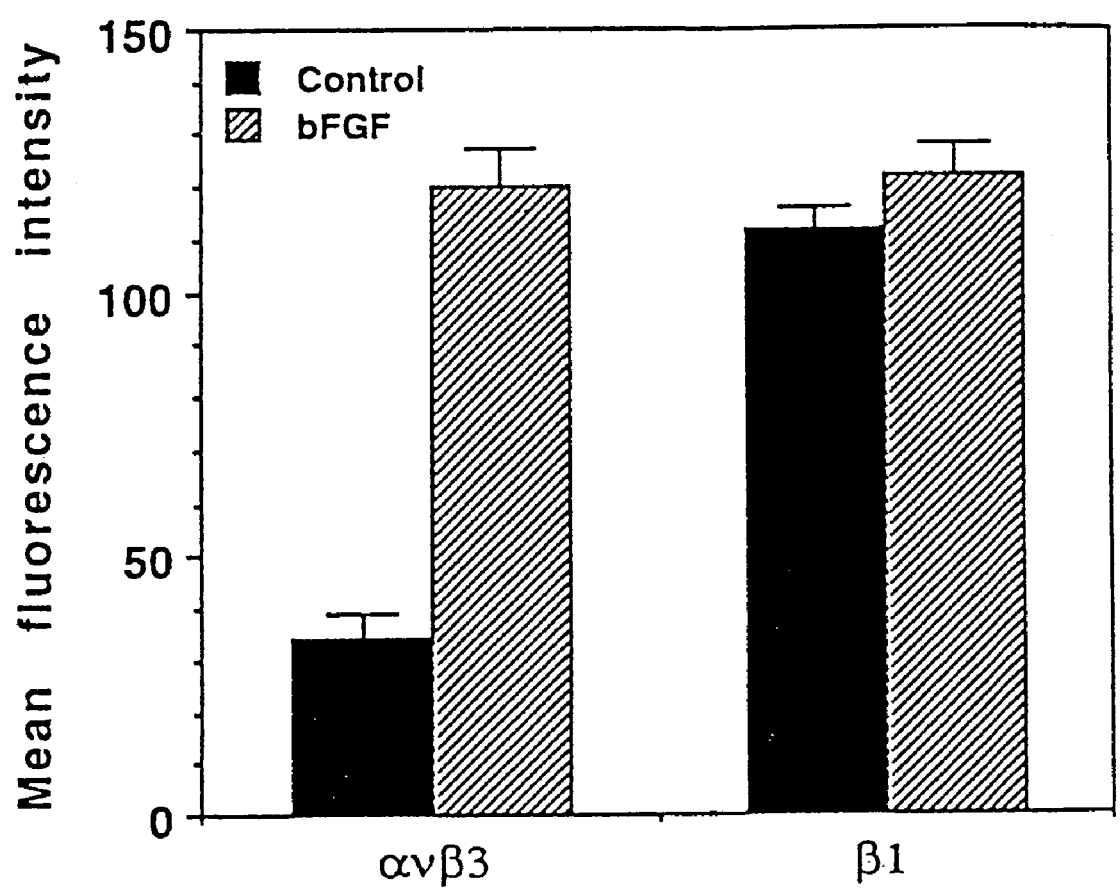
FIG. 6 illustrates the quantification in a bar graph of the relative expression of $\alpha_v\beta_3$ and $\beta_1$ in untreated and βFGF treated 10 day old CAMs as described in Example 6A. The mean fluorescence intensity is plotted on the Y-axis with the integrin profiles plotted on the X-axis.

The results plotted in FIG. 6 show that staining of $\alpha_v\beta_3$ was significantly enhanced (four times higher) on CAMs treated with βFGF as determined by the Wilcoxon Rank Sum Test (P<0.0001) whereas $\beta_1$ staining was not significantly different with βFGF treatment.

The CAM assay was further used to examine the effect of another potent angiogenesis inducer, tumor necrosis factor-alpha (TNFα), on the expression of $\beta_1$ and $\beta_3$ integrins. Filter disks impregnated with either βFGF or TNFα and placed on CAMs from 10 day embryos were found to promote local angiogenesis after 72 hours.

Figure 7A:
FIGS. 7A-7C illustrates the appearance of an untreated 10 day old CAM, a βFGF treated CAM, and a TNFα treated CAM, respectively, the procedures and results of which are described in Example 6A.
Figure 7B:
Figure 7C:

The results are shown in the photomicrographs of CAMs either untreated (FIG. 7A), treated with βFGF (FIG. 7B) or treated with TNFα (FIG. 7C). Blood vessels are readily apparent in both the βFGF and TNFα treated preparations but are not present in the untreated CAM. Thus, the topical application of a growth factor/cytokine resulted in the induction of angiogenesis from mature vessels in an adjacent area into the area originally devoid of blood vessels. In view of the βFGF-induced blood vessels and concomitant expression of $\alpha_v\beta_3$ as shown in FIG. 5C, treatment of TNFα results in comparable activities.

These findings indicate that in both human and chick, blood vessels involved in angiogenesis show enhanced expression of $\alpha_v\beta_3$. Consistent with this, expression of $\alpha_v\beta_3$ on cultured endothelial cells can be induced by various cytokines in vitro as described by Janat et al., *J. Cell Physiol.*, 151:588 (1992); Enenstein et al., Exp. Cell Res., 203:499 (1992) and Swerlick et al., *J. Invest. Derm.*, 99:715 (1993).

The effect on growth-factor induced angiogenesis by antibody and peptide inhibitors is presented in Examples 7A and 7B.

B. Embryonic Angiogenesis

The CAM preparation for evaluating the effect of angiogenesis inhibitors on the natural formation of embryonic neovasculature was the 6 day embryonic chick embryo as previously described. At this stage in development, the blood vessels are undergoing de novo growth and thus provides a useful system for determining if $\alpha_v\beta_3$ participates in embryonic angiogenesis. The CAM system was prepared as described above with the exception that the assay was performed at embryonic day 6 rather than at day 10. The effect on embryonic angiogenesis by treatment with antibodies and peptides of this invention are presented in Example 7C.

C. Angiogenesis Induced by Tumors

To investigate the role of $\alpha_v\beta_3$ in tumor-induced angiogenesis, $\alpha_v\beta_3$-negative human M21-L melanoma fragments were used in the CAM assay that were previously grown and isolated from the CAM of a 17-day chick embryo as described by Brooks et al., *J. Cell Biol.*, 122:1351 (1993) and as described herein. These fragments induced extensive neovascularization in the presence of buffer alone.

Angiogenesis was induced in the CAM assay system by direct apposition of a tumor fragment on the CAM. Preparation of the chick embryo CAM was identical to the procedure described above. Instead of a filter paper disks a 50 milligram (mg) to 55 mg in weight fragment of either human melanoma tumor M21L or human lung carcinoma tumor UCLAP-3, both of which are $\alpha_v\beta_3$ negative tumors, was placed on the CAM in an area originally devoid of blood vessels.

The M21L human melanoma cell line or the UCLAP-3 human lung carcinoma cell line, both $\alpha_v\beta_3$ negative, were used to grow the solid human tumors on the CAMs of chick embryos. A single cell suspension of 5×10⁶ M21L or UCLAP-3 cells were first applied to the CAMs in a total volume of 30 microliters (ul) of sterile HBSS. The windows were sealed with tape and the embryos were incubated for 7 days to allow growth of human tumor lesions. At the end of 7 days, now a 17-day embryo, the tumors were resected from the CAMs and trimmed free of surrounding CAM tissue. The tumors were sliced into 50 mg to 55 mg tumor fragments. The tumor fragments were placed on a new set of 10 day chick embryo CAMs as described in Example 6A in an area devoid of blood vessels.

These CAM tumor preparations were then subsequently treated as described in Examples 7D and 7E for measuring the effects of antibodies and peptides on tumor-induced angiogenesis.

7. Inhibition of Angiogenesis as Measured in the CAM Assay

A. Inhibition of Growth Factor-Induced Angiogenesis by Topical Application of Inhibitors 1) Treatment with Monoclonal Antibodies To determine whether $\alpha_v\beta_3$ plays an active role in angiogenesis, filter disks saturated with βFGF or TNFα were placed on CAMs then the monoclonal antibodies (also referred to as mAb), LM609 (specific for $\alpha_v\beta_3$), CSAT (specific for $\beta_1$) or P3G2 (specific for $\alpha_v\beta_5$) were added to the preparation.

Angiogenesis was induced on CAMs from 10 day chick embryos by filter disks saturated with βFGF. Disks were then treated with 50 ml HBSS containing 25 mg of mAb in a total volume of 25 ul of sterile HBSS at 0, 24, and 48 hours. At 72 hours, CAMs were harvested and placed in a 35 mm petri dish and washed once with 1 ml of phosphate buffered saline. The bottom side of the filter paper and CAM tissue was then analyzed under an Olympus stereo microscope, with two observers in a double-blind fashion. Angiogenesis inhibition was considered significant when CAMs exhibited >50% reduction in blood vessel infiltration of the CAM directly under the disk. Experiments were repeated four times per antibody, with 6 to 7 embryos per condition.

Figures 8A, 8B, 8C, 8D, 8E:
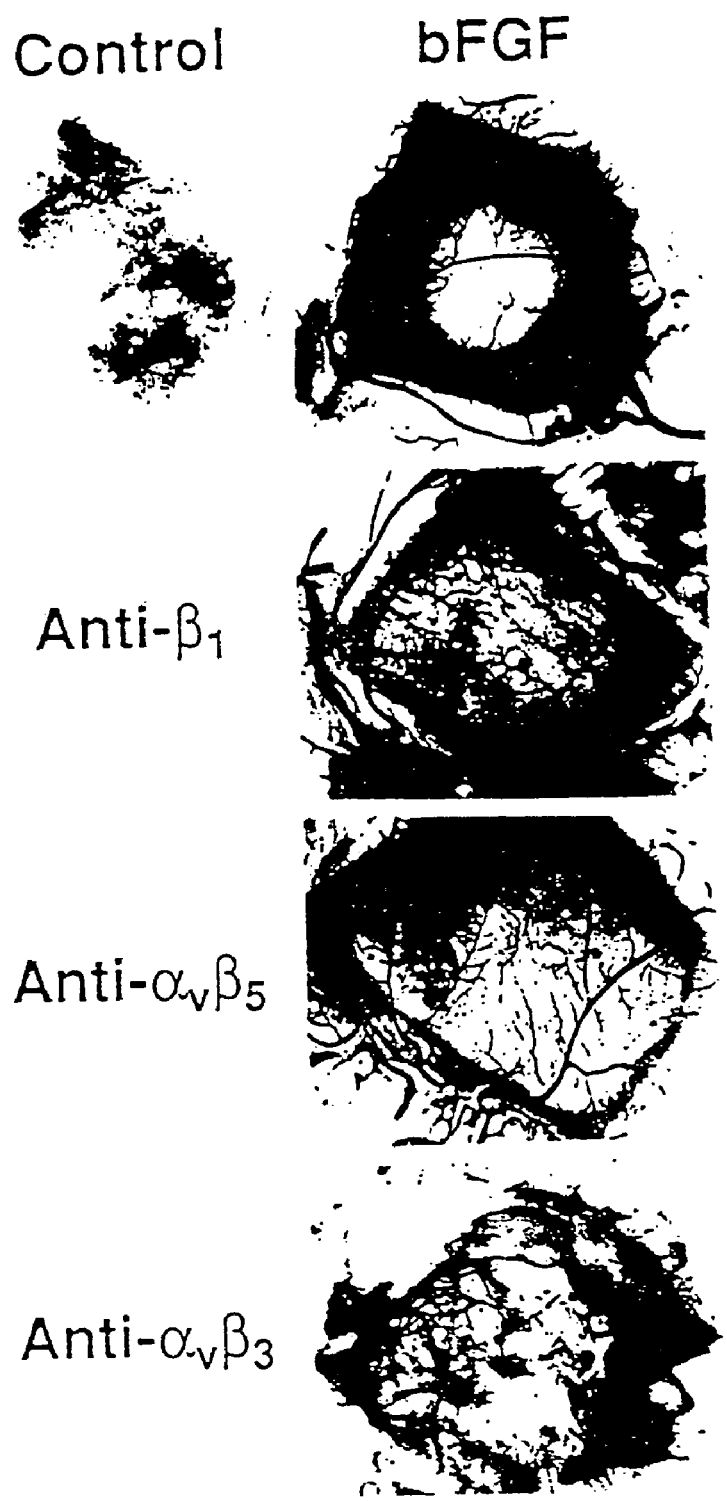
FIGS. 8A-8E illustrate the effect of topical antibody treatment on FGF-induced angiogenesis in a day 10 CAM as described in Example 7A1).

The results of the effects of mAb treatment on βFGF-induced angiogenesis is shown in FIGS. 8A-8B. An untreated CAM preparation devoid of blood vessels is shown in FIG. 8A to provide a comparison with the βFGF-blood vessel induction shown in FIG. 8B and effects thereon by the mAbs in FIGS. 8C-8E. About 75% of these CAMs treated with mAb LM609 exhibited >50% inhibition of angiogenesis as shown in FIG. 8E, and many of these appeared devoid of vessel infiltration. In contrast, the buffer control (FIG. 8A) and disks treated with mAbs CSAT (FIG. 8C) and P3G2 (FIG. 8D) consistently showed extensive vascularization.

Identical results were obtained when angiogenesis was induced with TNFα. To examine the effects of these same antibodies on preexisting mature blood vessels present from normal vessel development adjacent to the areas devoid of vessels, filter disks saturated with mAbs were placed on vascularized regions of CAMs from 10 day embryos that did not receive topical application of cytokine. None of the three mAbs affected preexisting vessels, as assessed by visualization under a stereo microscope. Thus, mAb LM609 selectively inhibited only new blood vessel growth and did not effect mature blood vessels present in adjacent areas. This same effect was seen with the application of synthetic peptides either applied topically or intravenously as described in Examples 7A2) and 7E2), respectively.

2) Treatment with Synthetic Peptides

CAM assays were also performed with the synthetic peptides of this invention to determine the effect of cyclic and linearized peptides on growth factor induced angiogenesis. The peptides were prepared as described in Example 1 and 80 ug of peptide was presented in a total volume of 25 ul of sterile HBSS. The peptide solution was applied to the CAM preparation immediately and then again at 24 and 48 hrs. At 72 hours the fiter paper and surrounding CAM tissue was dissected and viewed as described above.

Figure 9A:
FIGS. 9A-9C illustrate the effect of intravenous injection of synthetic peptide 66203 on angiogenesis induced by tumors as described in Example 7D2).
Figure 9B:
Figure 9C:

Results from this assay revealed were similar to those shown in FIGS. 9A-9C as described in Example 7E2) where synthetic peptides were intravenously injected into tumor induced blood vessels. Here, with the control peptide, 62186, the βFGF-induced blood vessels remained undisturbed as shown in FIG. 9A. In contrast when the cyclic RGD peptide, 62814, was applied to the filter, the formation of blood vessels was inhibited leaving the area devoid of new vasculature. This effect was similar in appearance to that shown in FIG. 9B as described in Example 7E2) below. In addition, also as shown in FIG. 9C for intravenously injected peptides, in areas in which mature blood vessels were present yet distant from the placement of the growth-factor saturated filter, no effect was seen with the topical treatment of synthetic peptides on these outlying vessels. The inhibitory activity of the peptides on angiogenesis thus is limited to the areas of angiogenesis induced by growth factors and does not effect adjacent preexisting mature vessels or result in any deleterious cytotoxicity to the surrounding area.

Similar assays are performed with the other synthetic peptides prepared in Example 1 and listed in Table 1.

B. Inhibition of Growth Factor-Induced Angiogenesis by Intravenous Application of Inhibitors 1) Treatment with Monoclonal Antibodies The effect on growth factor-induced angiogenesis with monoclonal antibodies intravenously injected into the CAM preparation was also evaluated for use in this invention.

The preparation of the chick embryo CAMs for intravenous injections were essentially as described in Example 7A with some modifications. During the candling procedures prominent blood vessels were selected and marks were made on the egg shell to indicate their positions. The holes were drilled in the shell and the CAMs were dropped and βFGF saturated filter papers were placed on the CAMs as described above. The windows were sealed with sterile tape and the embryos were replaced in the incubator. Twenty four hours later, a second small window was carefully cut on the lateral side of the egg shell directly over prominent blood vessels selected previously. The outer egg shell was carefully removed leaving the embryonic membranes intact. The shell membrane was made transparent with a small drop of mineral oil (Perkin-Elmer Corp, Norwalk, Conn.) which allowed the blood vessels to be visualized easily. Purified sterile MAbs, or synthetic peptides, the latter of which are described below, were inoculated directly into the blood vessels once with a 30 gauge needle at a dose of 200 ug of IgG per embryo in a total volume of 100 ul of sterile PBS. The windows were sealed with tape and the embryos were allowed to incubate until 72 hours. The filter disks and surrounding CAM tissues were analyzed as described before.

To determine the localization of LM609 mAb in CAM tissues or in tumor tissues, as shown herein and in the following Examples, that were previously inoculated intravenously with LM609, the fixed sections were blocked with 2.5% BSA in HBSS for 1 hour at room temperature followed by staining with a 1:250 dilution of goat anti-mouse rodamine labeled secondary antibody (Tango). The sections were then analyzed with a Zeiss immunofluorescence compound microscope.

The results of intravenous antibody treatment to the βFGF induced blood vessel CAM preparation are shown in FIGS. 10A-10C. In FIG. 10A, angiogenesis induced as a result of βFGF treatment is shown. No change to the presence of βFGF induced vasculature was seen with intravenous exposure to mAb P3G2, an anti-$\alpha_v\beta_5$ antibody, as shown in FIG. 10B. In contrast, treatment of the βFGF induced angiogenesis CAM preparation with LM609, an anti-$\alpha_v\beta_3$ antibody, resulted in the complete inhibition of growth of new vessels into the filter area as shown in FIG. 10C. The inhibitory effect on angiogenesis is thus resulting from the inhibition of $\alpha_v\beta_3$ receptor activity by the LM609 anti-$\alpha_v\beta_3$-specific antibody. Since the blocking of the $\alpha_v\beta_5$ does not inhibit the formation of neovasculature into the CAMs filter site, $\alpha_v\beta_5$ thus is not essential as compared to $\alpha_v\beta_3$ for growth of new vessels.

2) Treatment with Synthetic Peptides

The synthetic peptides prepared in Example 1 are separately intravenously injected into the growth factor induced blood vessels in the CAM preparation as described above. The effect of the peptides on the viability of the vessels is similarly assessed.

C. Inhibition of Embryonic Angiogenesis by Topical Application

1) Treatment with Monoclonal Antibodies

To determine whether $\alpha_v\beta_3$ participates in embryonic angiogenesis, the effect of LM609 on de novo growth of blood vessels on CAMs was examined in 6 day embryos, a stage marked by active neovascularization as described in Example 5A. The CAM assay was prepared as described in Example 6C with the subsequent topical application of disks saturated with mAbs placed on CAMs of 6 day old embryos in the absence of cytokines. After 3 days, CAMS were resected and photographed. Each experiment included 6 embryos per group and was repeated 2 times.

Figure 11A:
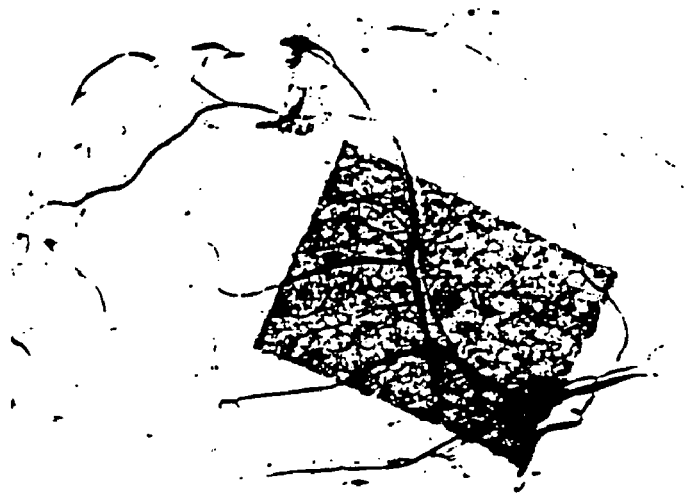
FIGS. 11A and 11C illustrate the effect on embryonic angiogenesis following topical application of anti-integrin antibodies as described in Example 7C. Angiogenesis was not inhibited by treatment of a 6 day CAM with anti-$\beta_1$ and anti-$\alpha_v\beta_5$ antibodies respectively shown in FIGS. 11A and 11B. In contrast, treatment with the anti-$\alpha_v\beta_3$ antibody LM609 resulted in the inhibition of blood vessel formation as shown in FIG. 11C.
Figure 11B:
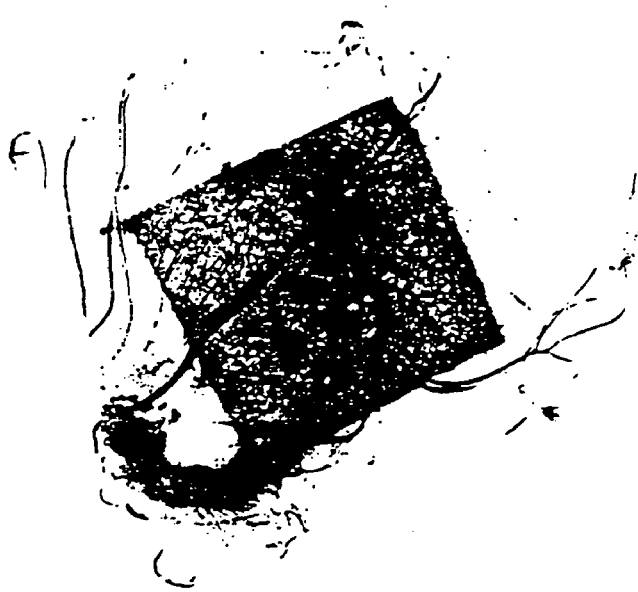
Figure 11C:
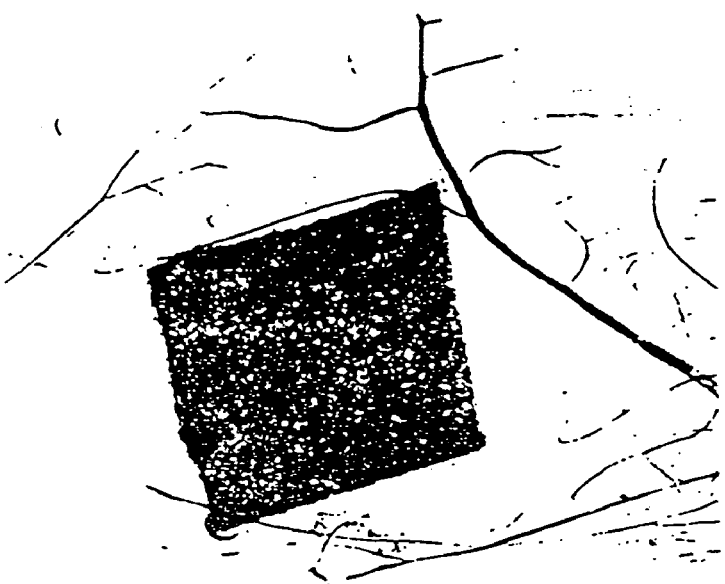

Antibody LM609 (FIG. 1C), but not CSAT (FIG. 11A) or P3G2 (FIG. 11B), prevented vascular growth under these conditions; this indicates that $\alpha_v\beta_3$ plays a substantial role in embryonic neovascularization that was independent of added growth factors for induction of angiogenesis.

2) Treatment with Synthetic Peptides

The synthetic peptides prepared in Example 1 are separately added to the embryonic CAM preparation prepared above and as described in Example 5A2) by either topical application to the CAM or intravenous application to blood vessels. The effect of the peptides on the viability of the vessels is similarly assessed.

D. Inhibition of Tumor-Induced Angiogenesis by Topical Application

1) Treatment with Monoclonal Antibodies

In addition to the angiogenesis assays described above where the effects of anti-$\alpha_v\beta_3$ antagonists, LM609 and peptides 62181, 62184, 62185, 62187 and 62880, on embryonic angiogenesis were evaluated, the role of $\alpha_v\beta_3$ in tumor-induced angiogenesis was also investigated. As an inducer, $\alpha_v\beta_3$-negative human M21-L melanoma fragments previously grown and isolated from the CAM of a 17-day chick embryo were used. The fragments were prepared as described in Example 6C.

As described above in Example 7A1), mAbs were separately topically applied to the tumor fragments at a concentration of 25 ug in 25 ul of HBSS and the windows were then sealed with tape. The mAbs were added again in the same fashion at 24 hours and 48 hours. At 72 hours, the tumors and surrounding CAM tissues were analyzed as described above in Example 7A1).

As described in Example 6C, tumors were initially derived by transplanting cultured M21-L cells, which do not to express integrin $\alpha_v\beta_3$ as described by Felding-Habermann et al., *J. Clin. Invest.*, 89:2018 (1992) onto the CAMs of 10-day old chick embryos. These $\alpha_v\beta_3$-negative fragments induced extensive neovascularization in the presence of buffer alone, or mAbs CSAT (anti-$\beta_1$) or P3G2 (anti-$\alpha_v\beta_5$). In contrast, mAb LM609 (anti-$\alpha_v\beta_3$) abolished the infiltration of most vessels into the tumor mass and surrounding CAM.

Figure 12:
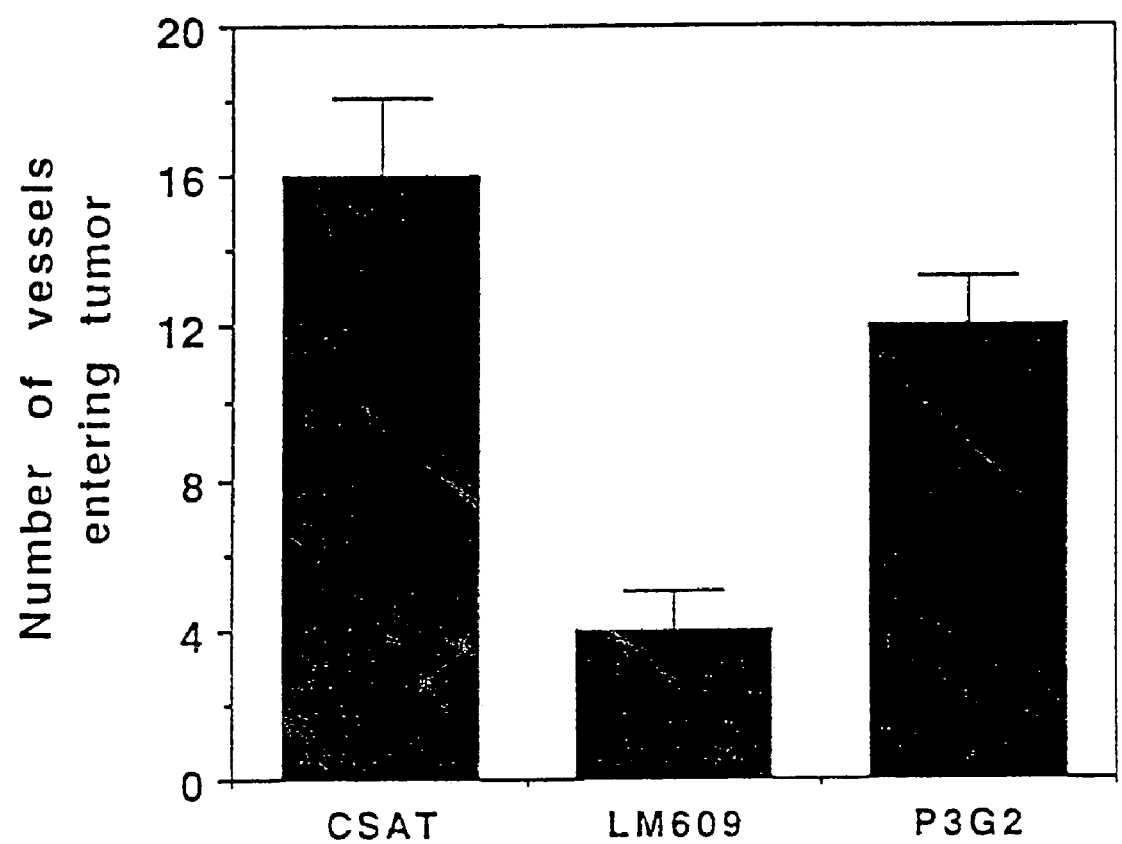
FIG. 12 illustrates the quantification of the number of vessels entering a tumor in a CAM preparation as described in Example 7D1). The graph shows the number of vessels as plotted on the Y-axis resulting from topical application of either CSAT (anti-$\beta_1$), LM609 (anti-$\alpha_v\beta_3$) or P3G2 (anti-$\alpha_v\beta_5$).

In order to quantitate the effect of the mAbs on the tumor-induced angiogenesis, blood vessels entering the tumor within the focal plane of the CAM were counted under a stereo microscope by two observers in a double-blind fashion. Each data bar presented in FIG. 12 represents the mean number of vessels±SE from 12 CAMs in each group representing duplicate experiments.

This quantitative analysis revealed a three-fold reduction in the number of vessels entering tumors treated with Mab LM609 compared to tumors treated with buffer or the other mAbs, P3G2 or CSAT (P<0.0001) as determined by Wilcoxon Rank Sum Test. The fact that M21-L tumors do not express $\alpha_v\beta_3$ indicates that mAb LM609 inhibits angiogenesis by directly affecting blood vessels rather than the tumor cells. These results correspond with the histological distribution of $\alpha_v\beta_3$ in cancer tissue biopsies shown in FIG. 3A-3D where the distribution of $\alpha_v\beta_3$ was limited to the blood vessels in the tumor and not to the tumor cells themselves.

2) Treatment with Synthetic Peptides

The synthetic peptides prepared in Example 1 are topically applied to the tumor-induced angiogenic CAM assay system as described above. The effect of the peptides on the viability of the vessels is similarly assessed.

E. Inhibition of Tumor-Induced Angiogenesis by intravenous Application

1) Treatment with Monoclonal Antibodies

Tumor-induced blood vessels prepared as described in Example 7D1) were also treated with mAbs applied by intravenous injection. Tumors were placed on the CAMs as described in Example 7D1) and the windows sealed with tape and 24 hours later, 200 ug of purified mAbs were inoculated once intravenously in chick embryo blood vessels as described previously. The chick embryos were then allowed to incubate for 7 days. The extent of angiogenesis was then observed as described in above. As described in Example 8 below, after this time period, the tumors were resected and analyzed by their weight to determine the effect of antibody exposure on tumor growth or suppression.

2) Treatment with Synthetic Peptides

The effects of peptide exposure to tumor-induced vasculature in the CAM assay system was also assessed. The tumor-CAM preparation was used as described above with the exception that instead of intravenous injection of a mAb, synthetic peptides prepared as described in Example 1 and Example 7A2) were separately intravenously injected into visible blood vessels.

The results of CAM assays with the cyclic peptide, 66203 containing the HCl salt, and control peptide, 62186, are shown in FIGS. 9A-9C. In FIG. 9A, the treatment with the control peptide did not effect the abundant large blood vessels that were induced by the tumor treatment to grow into an area originally devoid of blood vessels of the CAM. In contrast when the cyclic RGD peptide, 66203, an antagonist to $\alpha_v\beta_3$, was applied to the filter, the formation of blood vessels was inhibited leaving the area devoid of new vasculature as shown in FIG. 9B. The inhibitory effect of the RGD-containing peptide was specific and localized as evidenced by an absence of any deleterious effects to vessels located adjacent to the tumor placement. Thus, in FIG. 9C, when inhibitory peptides are intravenously injected into the CAM assay system, no effect was seen on the preexisting mature vessels present in the CAM in areas adjacent yet distant from the placement of the tumor. The preexisting vessels in this location were not affected by the inhibitory peptide that flowed within those vessels although the generation of new vessels from these preexisting vessels into the tumor mass was inhibited. Thus, synthetic peptides including 66203 and 62184, previously shown in ligand-receptor assays in Example 4 to be antagonists of $\alpha_v\beta_3$, have now been demonstrated to inhibit angiogenesis that is limited to vessels undergoing development and not to mature preexisting vessels. In addition, the intravenous infusion of peptides does not result in any deleterious cytotoxicity to the surrounding area as evidence by the intact vasculature in FIG. 9C.

Similar assays are performed with the other synthetic peptides prepared in Example 1 and listed in Table 1.

8. Inhibition of Tumor Tissue Growth with $\alpha_v\beta_3$ Antagonists

As described in Example 7D1), in addition to visually assessing the effect of anti-$\alpha_v\beta_3$ antagonists on growth factor or tumor induced angiogenesis, the effect of the antagonists was also assessed by measuring any changes to the tumor mass following exposure. For this analysis, the tumor-induced angiogenesis CAM assay system was prepared as described in Example 6C and 7D. At the end of the 7 day incubation period, the resulting tumors were resected from the CAMs and trimmed free of any residual CAM tissue, washed with 1 ml of phosphate buffer saline and wet weights were determined for each tumor. In addition, preparation of the tumor for microscopic histological analysis included fixing representative examples of tumors in Bulins Fixative for 8 hours and serial sections cut and H&E stained.

A. Topical Application

The results of typical human melanoma tumor (M21L) weights resulting from topical application of control buffer (HBSS), P3G2 (anti-$\alpha_v\beta_5$) or LM609 (anti-$\alpha_v\beta_3$) are listed in Table 4. A number of embryos were evaluated for each treatment with the average tumor weight in milligrams (mg) from each being calculated along with the SE of the mean as shown at the bottom of the table.

TABLE 4

| Embryo No. | mAb Treatment | Tumor Weight (mg) |
| --- | --- | --- |
| 1 | HBSS | 108 |
| 2 | | 152 |
| 3 | | 216 |
| 4 | | 270 |
| 5 | | 109 |
| 6 | | 174 |
| 1 | P3G2 | 134 |
| 2 | | 144 |
| 3 | | 408 |
| 4 | | 157 |
| 5 | | 198 |
| 6 | | 102 |
| 7 | | 124 |
| 8 | | 99 |
| 1 | LM609 | 24 |
| 2 | | 135 |
| 3 | | 17 |
| 4 | | 27 |
| 5 | | 35 |
| 6 | | 68 |
| 7 | | 48 |
| 8 | | 59 |

TABLE 4-continued

| mAb Treatment | Average Tumor Weight |
|---|---|
| HBSS control | 172 ± 26 |
| P3G2 | 171 ± 36 |
| LM609 | 52 ± 13 |

Exposure of a $\alpha_v\beta_3$-negative human melanoma tumor mass in the CAM assay system to LM609 caused the decrease of the untreated average tumor weight of 172 mg±26 to 52 mg±13. The P3G2 antibody had no effect on the tumor mass. Thus, the blocking of the $\alpha_v\beta_3$ receptor by the topical application of $\alpha_v\beta_3$-specific LM609 antibody resulted in a regression of tumor mass along with an inhibition of angiogenesis as shown in the preceding Examples. The measured diameter of the tumor mass resulting from exposure to P3G2 was approximately 8 millimeters to 1 centimeter on average. In contrast, the LM609-treated tumors were on average 2 to 3 millimeters in diameter.

Frozen sections of these tumors revealed an intact tumor cytoarchitecture for the tumor exposed to P3G2 in contrast to a lack or organized cellular structure in the tumor exposed to LM609. $\alpha_v\beta_3$ receptor activity is therefore essential for an $\alpha_v\beta_3$ negative tumor to maintain its mass nourished by development of $\alpha_v\beta_3$-expressing neovasculature. The blocking of $\alpha_v\beta_3$ with the $\alpha_v\beta_3$ antagonists of this invention results in the inhibition of angiogenesis into the tumor ultimately resulting in the diminution of tumor mass.

B. Intravenous Application

The results of typical carcinoma tumor (UCLAP-3) weights resulting from intravenous application of control buffer (PBS, phosphate buffered saline), CSAT (anti-$\beta_1$) or LM609 (anti-$\alpha_v\beta_3$) are listed in Table 5. A number of embryos were evaluated for each treatment with the average tumor weight from each being calculated along with the SE of the mean as shown at the bottom of the table.

TABLE 5

| Embryo No. | mAb Treatment | Tumor Weight |
|---|---|---|
| 1 | PBS | 101 |
| 2 | | 80 |
| 3 | | 67 |
| 4 | | 90 |
| 1 | CSAT | 151 |
| 2 | | 92 |
| 3 | | 168 |
| 4 | | 61 |
| 5 | | 70 |
| 1 | LM609 | 16 |
| 2 | | 54 |
| 3 | | 30 |
| 4 | | 20 |
| 5 | | 37 |
| 6 | | 39 |
| 7 | | 12 |

| mAb Treatment | Average Tumor Weight |
|---|---|
| PBS control | 85 ± 7 |
| CSAT | 108 ± 22 |
| LM609 | 30 ± 6 |

Exposure of a $\alpha_v\beta_3$-negative human carcinoma tumor mass in the CAM assay system to LM609 caused the decrease of the untreated average tumor weight of 85 mg±7 to 30 mg±6. The CSAT antibody did not significantly effect the weight of the tumor mass. Thus, the blocking of the $\alpha_v\beta_3$ receptor by the intravenous application of $\alpha_v\beta_3$-specific LM609 antibody resulted in a regression of a carcinoma as it did for the melanoma tumor mass above along with an inhibition of angiogenesis as shown in the preceding Examples. In addition, human melanoma tumor growth was similarly inhibited by intravenous injection of LM609.

Thus, the aforementioned Examples demonstrate that integrin $\alpha_v\beta_3$ plays a key role in angiogenesis induced by a variety of stimuli and as such $\alpha_v\beta_3$ is a valuable therapeutic target with the $\alpha_v\beta_3$ antagonists of this invention for diseases characterized by neovascularization.

The foregoing written specification is considered to be sufficient to enable one skilled in the art to practice the invention. The present invention is not to be limited in scope by the cell line deposited, since the deposited embodiment is intended as a single illustration of one aspect of the invention and any cell line that is functionally equivalent is within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A method of treating psoriasis in a patient comprising administering to said patient a therapeutically effective amount of an antibody immunospecific for $\alpha_v\beta_3$.

2. The method of claim 1, wherein said antibody is a monoclonal antibody.

3. The method of claim 1, wherein said antibody is a humanized antibody.

4. The method of claim 1, 2, or 3, wherein said antibody is an agent binding fragment.

5. The method of claim 1, wherein said administering comprises intravenous administration.

6. The method of claim 1, wherein said amount is from about 0.1 mg/kg to about 300 mg/kg patient body weight.

7. The method of claim 1, wherein said amount is from about 0.2 mg/kg to about 200 mg/kg patient body weight.

8. The method of claim 1, wherein said amount is from about 0.5 mg/kg to about 20 mg/kg patient body weight.

9. The method of claim 1, 2, or 3, wherein said antibody specifically binds $\alpha_v\beta_3$ complex.

10. The method of claim 1, 2, or 3, wherein said antibody is selective for $\alpha_v\beta_3$ over other integrins.

11. The method of claim 1, 2, or 3, wherein said antibody is selective for $\alpha_v\beta_3$ over $\alpha_v\beta_1$, $\alpha_v\beta_5$ and $\alpha_{IIb}\beta_3$.

* * * * *

SEQUENCE LISTING

<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: label=BOC-GRGDFV-OMe
    note="BOC signifies the N-terminal protecting
    group butyloxycarbonyl; OMe signifies a C-terminal
    methyl ester; arginine in the second position
<223> OTHER INFORMATION: label=OMe
    note="OMe signifies the C-terminal protecting
    group methyl ester."

-continued

```
<223> OTHER INFORMATION: label=D- Arg
      note="A prefix "D"in D-Arg signifies that the
      arginine in position 2 is a D-amino acid."
<220> FEATURE:
<223> OTHER INFORMATION: synthesized

<400> SEQUENCE: 1

Gly Arg Gly Asp Phe Val
1               5

<210> SEQ ID NO 2
<211> LENGTH: 6
<212> TYPE: PRT
<213> ORGANISM: Artificial Sequence
<220> FEATURE:
<223> OTHER INFORMATION: label=BOC
      note="BOC signifies the N-terminal blocking group
      tertbutyloxycarbonyl."
<223> OTHER INFORMATION: label=OH
      note="OH signifies a free C-terminal carboxylic
      acid."
<223> OTHER INFORMATION: label=D- Arg
      note="A prefix "D"in D-Arg signifies that the
      arginine in position 2 is a D-amino acid."
<220> FEATURE:
<223> OTHER INFORMATION: synthesized

<400> SEQUENCE: 2

Gly Arg Gly Asp Phe Val
1               5

<210> SEQ ID NO 3
<211> LENGTH: 6
<212> TYPE: PRT
<213> ORGANISM: Artificial Sequence
<220> FEATURE:
<223> OTHER INFORMATION: label=H
      note="H signifies a free N-terminal amine."
<223> OTHER INFORMATION: label=OH
      note="OH signifies a free C-terminal carboxylic
      acid."
<223> OTHER INFORMATION: label=D- Arg
      note="A prefix "D"in D-Arg at position 2,
      signifies that the arginine is a D-amino acid."
<220> FEATURE:
<223> OTHER INFORMATION: synthesized

<400> SEQUENCE: 3

Gly Arg Gly Asp Phe Val
1               5

<210> SEQ ID NO 4
<211> LENGTH: 6
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 4

Gly Arg Gly Asp Phe Val
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 5

Arg Gly Asp Phe Val
1               5

<210> SEQ ID NO 6
<211> LENGTH: 5
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 6

Arg Ala Asp Phe Val
1               5

<210> SEQ ID NO 7
<211> LENGTH: 5
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 7

Arg Gly Asp Phe Val
1               5

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Tyr Thr Ala Glu Cys Lys Pro Gln Val Thr Arg Gly Asp Val Phe
1               5                   10                  15

<210> SEQ ID NO 9
<211> LENGTH: 5
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 9

Arg Ala Asp Phe Val
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 10

Ala Arg Gly Asp Phe Leu
1               5

<210> SEQ ID NO 11
<211> LENGTH: 6
<212> TYPE: PRT
<213> ORGANISM: Artificial Sequence
<220> FEATURE:
<223> OTHER INFORMATION: label=cyclo
      note="Cyclo signifies a cyclic peptide; lower case
      letters indicate a D-amino acid; capital letters
      indicate a L-amino acid."
<220> FEATURE:
<223> OTHER INFORMATION: synthesized

<400> SEQUENCE: 11

Gly Arg Gly Asp Phe Leu
1               5

<210> SEQ ID NO 12
<211> LENGTH: 12
<212> TYPE: PRT
<213> ORGANISM: Artificial Sequence
<220> FEATURE:
<223> OTHER INFORMATION: synthesized

<400> SEQUENCE: 12

Thr Arg Gln Val Val Cys Asp Leu Gly Asn Pro Met
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthesized

<400> SEQUENCE: 13

Gly Val Val Arg Asn Asn Glu Ala Leu Ala Arg Leu Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: synthesized

<400> SEQUENCE: 14

Thr Asp Val Asn Gly Asp Gly Arg His Asp Leu
1               5                   10

<210> SEQ ID NO 15
<211> LENGTH: 5
```

```
-continued
<212> TYPE: PRT
<213> ORGANISM: Artificial Sequence
<220> FEATURE:
<223> OTHER INFORMATION: synthesized

<400> SEQUENCE: 15

Gly Arg Gly Asp Ser
1               5
```